US008008297B2

(12) United States Patent
Stranix et al.

(10) Patent No.: US 8,008,297 B2
(45) Date of Patent: Aug. 30, 2011

(54) LYSINE BASED COMPOUNDS

(75) Inventors: Brent Richard Stranix, Pointe-Claire (CA); Valerie Perron, Laval (CA)

(73) Assignee: Ambrilia Biopharma Inc., Verdun, Quebec (CA)

( * ) Notice: Subject to any disclaimer, the term of this patent is extended or adjusted under 35 U.S.C. 154(b) by 534 days.

(21) Appl. No.: 12/078,760

(22) Filed: Apr. 4, 2008

(65) Prior Publication Data

US 2008/0269172 A1 Oct. 30, 2008

Related U.S. Application Data

(63) Continuation of application No. 10/902,935, filed on Aug. 2, 2004, now Pat. No. 7,388,008.

(51) Int. Cl.
*A61K 31/4406* (2006.01)
*A61K 31/221* (2006.01)
*C07D 215/22* (2006.01)

(52) U.S. Cl. ............. 514/237.5; 544/148; 544/159; 544/406; 546/316; 546/323; 548/333.5; 548/537; 549/438; 549/487; 560/10; 560/13; 562/427; 562/430; 564/85; 514/90; 514/117; 514/351

(58) Field of Classification Search .................... None
See application file for complete search history.

(56) References Cited

U.S. PATENT DOCUMENTS

| | | | |
|---|---|---|---|
| 5,013,861 A | 5/1991 | Weller, III et al. |
| 5,527,829 A | 6/1996 | Kalish |
| 5,614,522 A | 3/1997 | Talley et al. |
| 5,714,605 A | 2/1998 | Vazquez et al. |
| 5,776,718 A | 7/1998 | Palmer et al. |
| 5,965,588 A | 10/1999 | Vazquez et al. |
| 5,985,870 A | 11/1999 | Getman et al. |
| 6,022,994 A | 2/2000 | Vazquez et al. |
| 6,127,372 A | 10/2000 | Tung et al. |
| 6,159,995 A | 12/2000 | Thorwart et al. |
| 6,384,036 B1 | 5/2002 | Freskos et al. |
| 6,436,989 B1 | 8/2002 | Hale et al. |
| 6,455,587 B1 | 9/2002 | Bouzide et al. |
| 6,506,786 B2 | 1/2003 | Stranix et al. |
| 6,528,532 B1 | 3/2003 | Stranix et al. |
| 6,656,965 B2 | 6/2003 | Stranix et al. |
| 6,608,100 B1 | 8/2003 | Stranix et al. |
| 6,610,689 B2 | 8/2003 | Stranix et al. |
| 6,632,816 B1 | 10/2003 | Stranix et al. |
| 6,677,367 B2 | 10/2003 | Stranix et al. |
| 6,703,403 B2 | 3/2004 | Norbeck et al. |
| 7,388,008 B2 | 6/2008 | Stranix et al. |
| 2006/0025592 A1 | 2/2006 | Stranix et al. |
| 2006/0287316 A1 | 12/2006 | Wu et al. |
| 2009/0253926 A1 | 10/2009 | Milot et al. |
| 2010/0130765 A1 | 5/2010 | Milot et al. |

FOREIGN PATENT DOCUMENTS

| | | |
|---|---|---|
| CA | 2 089 747 | 4/1992 |
| CA | 2 077 948 | 3/1993 |
| CA | 2 316 218 A1 | 7/1999 |
| CA | 2 440 931 | 8/2002 |
| EP | 0532466 | 3/1993 |
| EP | 0 763 017 | 3/1997 |
| JP | 06321950 | 11/1994 |
| JP | 6321950 | 11/1994 |
| WO | WO 92/06998 | 4/1992 |
| WO | WO 95/06998 | 3/1995 |
| WO | WO-95/24385 | 9/1995 |
| WO | WO-97/27180 | 7/1997 |
| WO | WO-98/31664 | 7/1998 |
| WO | WO 99/33815 | 7/1999 |
| WO | WO-99/55687 A2 | 11/1999 |
| WO | WO-00/47551 | 8/2000 |
| WO | WO-00/76961 | 12/2000 |
| WO | WO-01/68593 A2 | 9/2001 |
| WO | WO-02/064551 A2 | 8/2002 |
| WO | WO-03/074467 | 9/2003 |
| WO | WO-2004/054586 | 7/2004 |
| WO | WO-2004/056764 | 7/2004 |
| WO | WO-2005/066131 | 7/2005 |
| WO | WO-2006/012725 | 2/2006 |
| WO | WO-2006/114001 | 11/2006 |
| WO | WO-2007/062526 | 6/2007 |

OTHER PUBLICATIONS

Anderson, et al., The use of esters of N-Hydroxysuccinimide in peptide synthesis, *J. Am. Chem. Soc.*, 86:1839-1842 (1964).
Andrade, et al., HIV-related drug metabolism and cytochrome P450 enzymes, *AIDS Clin. Care*, 12(11):91-95 (2000).
Bouzide, et al., Lysine derivatives as potent HIV protease inhibitors. Discovery, synthesis and structure-activity relationship studies, *Bioorg. Med. Chem. Lett.* 15 (2005) 1509-1513.
Boyle, et al., Asymmetric transformation of α-amino-ε-caprolactam, a lysine precursor, *J. Org. Chem.*, 44(26):4841-4847 (1979).
Bukrinsky, et al., Active nuclear import of human immunodeficiency virus type 1 preintegration complexes, *Proc. Natl. Acad. Sci. USA*, 89(14):6580-6584 (1992).
Calogeropoulou, et al., Strategies in the design of prodrugs of anti-HIV agents, *Current Topics in Medicinal Chemistry*, 3(13):1467-1495 (2003).
*Chemical Abstracts*, 123(7), Abstract 83099w (1995), Harada and Mikio, *Jpn. Kokai Tokkyo Koho JP* 06,321,950, Takeda Chemical Industries, LTD. (1994).

(Continued)

*Primary Examiner* — Zinna Northington Davis
(74) *Attorney, Agent, or Firm* — Clark & Elbing LLP

(57) ABSTRACT

The present invention provides lysine based compounds of the formula;

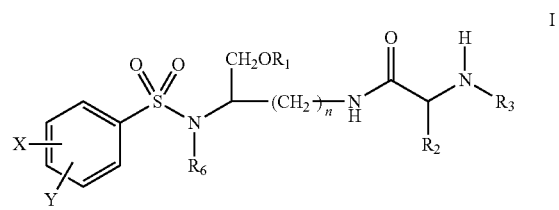

and when the compound of formula I comprises an amino group, pharmaceutically acceptable ammonium salts thereof, wherein $R_1$ may be, for example, $(HO)_2P(O)$—, $(NaO)_2P(O)$—, alkyl-CO— or cycloalkyl-CO—, wherein X may be, for example, F, Cl, and Br, and wherein $R_2$ and $R_3$ are as defined herein.

23 Claims, No Drawings

OTHER PUBLICATIONS

*Chemical Abstracts*, 46(13), Abstract 6593c (1952), Izumiya, *J. Chem. Soc. Japan, Pure Chem. Sect.*, 72(1):149-152 (1951).

*Chemical Abstracts*, 46(13), Abstract 6593g (1952), Izumiya, *J. Chem. Soc. Japan, Pure Chem. Sect.*, 72(5):445-447 (1951).

*Chemical Abstracts*, 46(13), Abstract 6593i (1952), Izumiya, *J. Chem. Soc. Japan, Pure Chem. Sect.*, 72(6):550-552 (1951).

*Chemical Abstracts*, 62(2), Abstract 1740c (1965), Hermann, et al., *Peptides Proc. European Symp., 5th, Oxford*, 171-175 (1962).

Dandache, et al., In vitro antiviral activity and cross-resistance profile of PL-100, a novel protease inhibitor of Human Immunodeficiency Virus Type 1, Antimicrob. Agents Chemother., 51(11):4036-4043 (2007).

Dankwardt, et al., Amino acid derived sulfonamide hydroxamates as inhibitors of procollagen C-Proteinase. Part 2: Solid-phase optimization of side chains, *Bioorg. Med. Chem. Lett.* 12, 2002, 1233-1235.

El-Naggar, et al., Synthesis and biological activity of some new quinoline-8-sulphonylamino acid and dipeptide derivatives, *Acta Pharm. Jugosl.*, 33(2):103-110 (1983), XP000926585.

El-Naggar, et al., Synthesis of nitrobenzene- and nitrotoluenesulfonylamino acid and dipeptide derivatives, *Pol. J. Chem.*, 52(3):637-642 (1978), XP000926586.

Elmore, et al., Kinetics and mechanism of catalysis by proteolytic enzymes, *Biochem. J.*, 102:728-734 (1967).

Ettmayer, et al., Lessons learned from marketed and investigational prodrugs, *Journal of Medicinal Chemistry*, 47(10):2393-2404 (2004).

Fitzsimmons, et al., Selective biotransformation of the human immunodeficiency virus protease inhibitor Saquinavir by human small-intestinal Cytochrome P4503A4, *Drug Metab. Disp.*, 25(2):256-266 (1997).

Gallay, et al., HIV-1 infection of nondividing cells: C-terminal tyrosine phosphorylation of the viral matrix protein is a key regulator, *Cell*, 80(3):379-388 (1995).

Garrity, et al., A new synthetic route to 2-(p-nitrobenzyl)-1,4,7,10-Tetraazacyclododecane, *Tetrahedron Letters*, 34(35):5531-5534 (1993).

Goff, Retroviral reverse transcriptase: Synthesis, structure, and function, *Journal of Acquired Immune Deficiency Syndromes*, 3(8):817-831(1990).

Greene and Wuts, Protection for the amino group, *Protective Groups in Organic Synthesis*, 3rd Ed., 518-525 (John Wiley & Sons, Inc., 1999).

Greene, Protection for the amino group, *Protective Groups in Organic Synthesis*, 258-263 (John Wiley & Sons, Inc., 1981).

Hamill, et al., Non-peptide fibrinogen receptor antagonists. Synthesis of [$^3$H]L-756,568, *J. Labelled Cpd. Radiopharm.*, 42(6):605-609 (1999), XP000926587.

Haseltine, Molecular biology of the human immunodeficiency virus type 1, *The FASEB Journal*, 5(10):2349-2360 (1991).

Hlavacek, et al., An alternative route to N$^\alpha$-methylamino acid derivatives: Synthesis and conformation of some N$^\alpha$-acetyl-N$^\alpha$-methylamino acid methylamides, *Collection Czech. Chem. Commun.*, 53:2473-2494 (1988), XP001002995.

Japour, et al., Standardized peripheral blood mononuclear cell culture assay for determination of drug susceptibilities of clinical human immunodeficiency virus type 1 isolates, *Antimicrobial Agents and Chemotherapy*, 37(5):1095-1101 (1993).

Karup, et al., 9-acridinylpeptides and 9-acridinyl-4-nitrophenylsulfonylpeptides, *Int. J. Peptide Protein Res.*, 32(5):331-343 (1988), XP000926584.

Kempf, et al., Pharmacokinetic enhancement of inhibitors of the human immunodeficiency virus protease by coadministration with Ritonavir, *Antimicrob. Agents Chemother.*, 41(3):654-660 (1997).

Kolc, Amino acids and peptides, *Collect. Czech. Chem. Commun.*, 34(2):630-634 (1969).

Kottirsch, et al., Beta-amino acid derivatives as orally active non-peptide fibrinogen receptor antagonists, *Bioorg. Med. Chem. Lett.*, 7 (1997) 727-732, XP004136118.

Lasky, et al., Delineation of a region of the human immunodeficiency virus Type 1 gp120 glycoprotein critical for interaction with the CD4 receptor, *Cell*, 50(6):975-985 (1987).

Leclerc, et al., On the selectivity of acylation of unprotected diamino acids, *Can. J. Chem.*, 46(7):1047-1051 (1968), XP000926722.

Lescrinier, et al., $\alpha$-Amino acids derived from ornithine as building blocks for peptide synthesis, *J. Peptide Res.*, 49(2):183-189 (1997), XP000679594.

Maeda, et al., Amino acids and peptides. V. Synthesis of amino acid derivatives containing a sulfonamide bond, *Chem. Pharm. Bull.*, 33(5):2137-2141 (1985), XP001010687.

Matayoshi, et al., Novel fluorogenic substrates for assaying retroviral proteases by resonance energy transfer, *Science*, 247(4945):954-958 (1990).

Meek, et al., Inhibition of HIV-1 protease in infected T-lymphocytes by synthetic peptide analogues, *Nature*; 343(6253):90-92 (1990).

Pauwels, et al., Rapid and automated tetrazolium-based colorimetric assay for the detection of anti-HIV compounds, *J. Virological Methods*, 20(4):309-321 (1988).

Poduska, et al., Amino acids and peptides. LII. Intramolecular aminolysis of amide bonds in derivatives of $\alpha,\gamma$-Diaminobutyric acid, $\alpha,\beta$-Diaminopropionic acid, and ornithine, *Coll. Czech. Chem. Commun.*, 30(7):2410-2433 (1965).

Sakai, et al., Integration is essential for efficient gene expression of human immunodeficiency virus Type 1, *J. Virol.*, 67(3):1169-1174 (1993).

Schon, et al., 9-fluorenylmethyl pentafluorophenyl carbonate as a useful reagent for the preparation of N-9-fluorenylmethyloxycarbonylamino acids and their pentafluorophenyl esters, *J. of Synthetic Org. Chem.*, 4:303-305, (1986), XP002182716.

Sevigny, et al., Antiviral activity and cross-resistance profile of P-1946, a novel human immunodeficiency virus type 1 protease inhibitor, Antiviral Res. 70(2):17-20 (2006).

Solinas, et al., The oxidative deamination of I-aminoethylcysteine sulfoxide and sulfone by snake venom I-amino acid oxidase, *Physiol. Chem. Phys. Med. NMR*, 25(4):281-285 (1993).

Stranix, et al., Lysine sulfonamides as novel HIV-protease inhibitors: Nε-Acyl aromatic α-amino acids, Bioorg. Med. Chem. Lett. 16 (2006) 3459-3462.

Treluyer, et al., Oxidative metabolism of Amprenavir in the human liver. Effect of the CYP3A maturation, *Drug Metab. Disp.*, 31(3):275-281 (2003).

Vierling, et al., Prodrugs of HIV protease inhibitors, *Current Pharmaceutical Design*, 9(22):1755-1770 (2003).

Chong et al., "Peptidomimetic HIV Protease Inhibitors: Phosphate Prodrugs with Improved Biological Acitivities," *J. Med. Chem.* 36(17):2575-2577, 1993.

Sohma et al., "Development of Water-Soluble Prodrugs of the HIV-1 Protease Inhibitor KNI-727: Importance of the Conversion Time for Higher Gastrointestinal Absorption of Prodrugs Based on Spontaneous Chemical Cleavage," *J. Med. Chem.* 46(19):4124-4135, 2003.

International Search Report for PCT/CA2001/00296, dated Nov. 27, 2001, mailed Dec. 10, 2001.

International Search Report for PCT/CA2004/001440, dated Nov. 27, 2004, mailed Dec. 10, 2004.

Written Opinion for PCT/CA2004/001440, mailed Dec. 10, 2004.

European Search Report for EP 08021798.7 dated May 12, 2010.

European Examination Report for EP 08021798.7 dated May 25, 2010.

LYSINE BASED COMPOUNDS

This application is a continuation of U.S. application Ser. No. 10/902,935, now U.S. Pat. No. 7,388,008 filed Aug. 2, 2004.

TECHNICAL FIELD OF THE INVENTION

This invention relates to lysine based compounds which present good solubility, and bioavailability. More particularly, the present invention relates to lysine based compounds having a physiologically cleavable unit, whereby upon cleavage of the unit, the compound is able to release an HIV protease inhibitor. The compounds and pharmaceutical compositions of the present invention are particularly well suited for decreasing the pill burden and increasing patient compliance.

BACKGROUND OF THE INVENTION

Inhibitors of the HIV viral protease have been developed relatively recently and their use began only in 1996. Currently, they are considered the most effective drugs against HIV infection. Unfortunately, most current proteases inhibitors are relatively large hydrophobic molecules that possess rather low bioavailability. A high pill burden is therefore required to attain the therapeutic dose in a patient. This is a deterrent, which too often results in patient non-compliance and inadequate treatment results. This situation leads to sub-optimal therapeutic drug concentration that in turns leads to the development of HIV resistant strains. Consequently, there is an urgent need to improve the solubility and bioavailability of proteases inhibitors.

Examples of improved compounds have been developed in the form of prodrugs of aspartyl protease inhibitors such as described, for example, in U.S. Pat. No. 6,436,989 to Hale et al, the entire content of which is incorporated herein by reference. This patent shows a novel class of molecules characterized by favourable aqueous solubility, high oral bioavailability and facile in vivo generation of the active ingredient. However, it is well known that HIV has the ability to develop resistance to the currently available drugs. Thus, there is a need for alternative HIV protease inhibitors active towards wild-type and resistant viral strains. Thus, molecules derived from current HIV protease inhibitors showing enhanced solubility and bioavailability is desirable to fight resistant viral strains.

A unique class of aromatic derivatives which are inhibitors of aspartyl proteases is described in U.S. Pat. No. 6,632,816 to Stranix et al, the entire content of which is incorporated herein by reference. This patent includes, more particularly, N,-synthetic amino acid substituted L-lysine derivatives possessing potent aspartyl protease inhibitory properties. However, it would be advantageous to improve these derivatives by enhancing aqueous solubility and bioavailability in order to reduce the pill burden and to favour patient's compliance. Since it is challenging to generate active protease inhibitors, specifically toward wild-type and resistant strains, the formation of derivatives of original HIV protease inhibitors such as inhibitors described in U.S. Pat. No. 6,632,816 to Stranix et al, known to be active toward resistant strains represents a viable route with considerable advantages. More particularly, generation of compounds with enhanced aqueous solubility, bioavailability, time of duration and formulation properties along with other advantages is desirable in the development of an effective drug.

SUMMARY OF THE INVENTION

The present invention provides novel lysine based compounds originating from a class of derivatives that are potent aspartyl protease inhibitors and pharmaceutically acceptable derivatives thereof. These compounds may readily be cleaved in vivo to release the active ingredient. The active ingredient has an affinity for aspartyl proteases, in particular, HIV-1 aspartyl protease (U.S. Pat. No. 6,632,816). The active ingredients also present potent antiviral activity when tested on non-mutated HIV-1 viral strain (NL4.3 as the wild type virus) as well as several mutant strains. Therefore, the compounds of the present invention may be useful as a mean to increase solubility and improving bioavailability of the active ingredient (protease inhibitor). The compounds of the present invention may be used alone or in combination with other therapeutic or prophylactic agents for the treatment or prophylaxis of HIV infection. The compounds of the present invention possess good solubility and bioavailability and may be orally administered as aqueous solution.

It is the main objective of this invention to provide an improved class of lysine based compounds that are able to release an aspartyl protease inhibitor, and particularly, HIV aspartyl protease inhibitors. Lysine based compounds of the present invention may have a cleavable unit, whereby upon cleavage of the unit the compound is able to release an HIV protease inhibitor. The present invention also provides pharmaceutical compositions comprising lysine based compounds described herein.

Therefore the present invention provides in one aspect thereof, lysine based compounds which upon in vivo physiological conditions (e.g., metabolic, enteric and/or gastrointestinal conditions, etc.) allow the release of a protease inhibitor (e.g., aspartyl protease inhibitor). The compounds of the present invention may serve as means for improving the solubility and/or bioavailability of the protease inhibitors and therefore may reduce the pill burden and may favour patient's compliance.

The compounds of the present invention may have, for example, a (e.g., physiologically) cleavable (e.g., hydrolysable) bond or unit which upon cleavage of the cleavable bond or unit generates a protease inhibitor (e.g., an active protease inhibitor).

The protease inhibitor may act on a spartyl protease of HIV-1 including mutated and n on-mutated HIV-1 viral strain (e.g., NL4.3) or on protease of HIV-2 (mutated or non-mutated) or even on protease of related virus (SIV, etc.). The compounds of the present invention may be used alone or in combination with other therapeutic or prophylactic agents for the treatment or prophylaxis of, for example, an HIV infection.

The compounds and the pharmaceutical compositions of the present invention may release the protease inhibitor (active ingredient) in vivo and thereby may inhibit (e.g., in vivo) the activity of HIV aspartyl protease, an enzyme essential for virus maturation and infectivity. The compounds and the pharmaceutical compositions of the present invention may possess higher bioavailability and may also be apt to reduce dosages needed for inhibition and consequently may improve treatment of HIV-infected patients.

The present invention in accordance with one aspect thereof provides a compound (e.g. a compound able to generate an HIV protease inhibitor) of formula I:

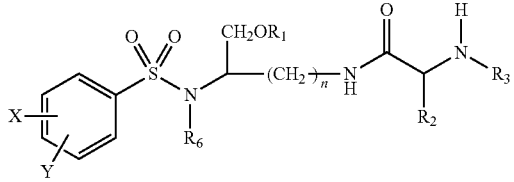

I pharmaceutically acceptable salts and derivatives thereof (e.g., for example, when the compound of the present invention comprises an amino group, the pharmaceutically acceptable salt may be an ammonium salt), wherein n may be, for example, 3 or 4, wherein X and Y, the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —CF$_3$, —OCF$_3$, —CN, —NO$_2$, —NR$_4$R$_5$, —NHCOR$_4$, —OR$_4$, —SR$_4$, —COOR$_4$, —COR$_4$, and —CH$_2$OH or X and Y together define an alkylenedioxy group selected from the group consisting of a methylenedioxy group of formula —OCH$_2$O— and an ethylenedioxy group of formula —OCH$_2$CH$_2$O—, wherein R$_6$ may be selected, for example, from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof, wherein R$_3$ may be selected, for example, from the group consisting of H, a straight alkyl group of 1 to 6 carbon atoms, a branched alkyl group of 3 to 6 carbon atoms, a cycloalkyl group of 3 to 6 carbon atoms, and a group of formula R$_{3A}$—CO—, wherein R$_{3A}$ may be selected, for example, from the group consisting of a straight or branched alkyl group of 1 to 6 carbon atoms (e.g. methyl, ethyl-, propyl, iso-propyl, butyl, iso-butyl, tert-butyl, tert-butyl-CH$_2$—, etc.), a cycloalkyl group having 3 to 6 carbon atoms (e.g. cyclopropyl-, cyclohexyl- etc.), a cycloalkylalkyl group having 3 to 6 carbon atoms in the cycloalkyl part thereof and 1 to 3 carbon atoms in the alkyl part thereof, (e.g. cyclopropyl-CH$_2$—, cyclohexyl-CH$_2$—, etc.), an alkyloxy group of 1 to 6 carbon atoms (e.g. CH$_3$O—, CH$_3$CH$_2$O—, iso-butylO-, tert-butylO-(Boc), etc.), tetrahydro-3-furanyloxy, —CH$_2$OH, —CF$_3$, —CH$_2$CF$_3$, —CH$_2$CH$_2$CF$_3$, ppyrrolidinyl, piperidinyl, 4-morpholinyl, CH$_3$O$_2$C—, CH$_3$O$_2$CCH$_2$—, Acetyl-OCH$_2$CH$_2$—, HO$_2$CCH$_2$—, 3-hydroxyphenyl, 4-hydroxyphenyl, 4-CH$_3$OC$_6$H$_4$CH$_2$—, CH$_3$NH—, (CH$_3$)$_2$N—, (CH$_3$CH$_2$)$_2$N—, (CH$_3$CH$_2$CH$_2$)$_2$N—, HOCH$_2$CH$_2$NH—, CH$_3$OCH$_2$O—, CH$_3$OCH$_2$CH$_2$O—, C$_6$H$_5$CH$_2$O—, 2-pyrrolyl, 2-pyridyl, 3-pyridyl, 4-pyridyl-, 2-pyrazinyl, 2-quinolyl, 3-quinolyl, 4-quinolyl, 1-isoquinolyl, 3-isoquinolyl, 2-quinoxalinyl, a phenyl group of formula

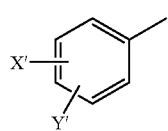

a picolyl group selected from the group consisting of

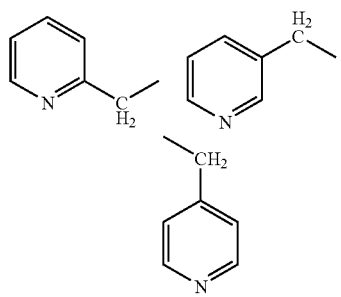

and a picolyloxy group selected from the group consisting of

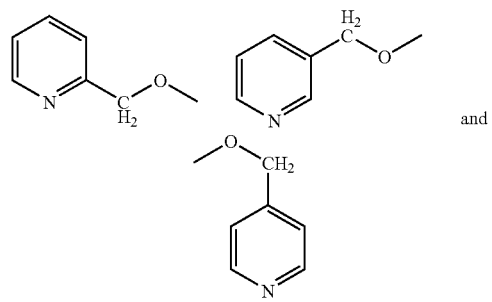

and a substituted pyridyl group selected from the group consisting of

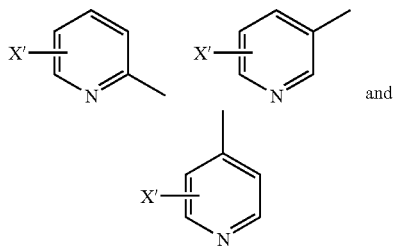

and and a group of formula,

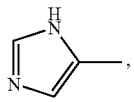

wherein X' and Y', the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —CF$_3$, —NO$_2$, —NR$_4$R$_5$, —NHCOR$_4$, —OR$_4$, —SR$_4$, —COOR$_4$, —COR$_4$ and —CH$_2$OH, wherein R$_4$ and R$_5$, the same or different, may be selected, for example, from the group consisting of H, a straight alkyl group of 1 to 6 carbon atoms, a branched alkyl group of 3 to 6 carbon atoms, and a cycloalkyl group of 3 to 6 carbon atoms, wherein R$_2$ may be selected, for example, from the group consisting of a diphenylmethyl group of formula IV

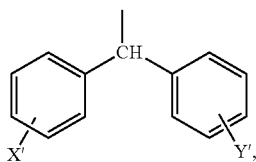

a naphthyl-1-CH$_2$— group of formula V

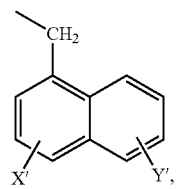

a naphthyl-2-CH$_2$— group of formula VI

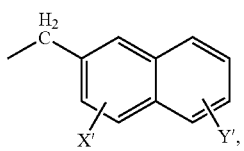

a biphenylmethyl group of formula VII

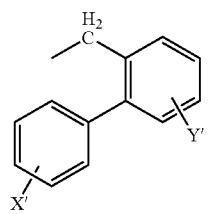

and an anthryl-9-CH$_2$— group of formula VIII

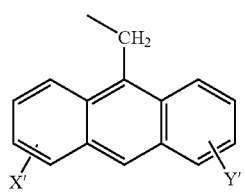

and wherein R$_1$ may be a cleavable unit (e.g., a physiologically cleavable unit), whereby upon cleavage of the unit, the compound releases a protease inhibitor (an HIV protease inhibitor), provided that R$_1$ is not H. For example, R$_1$ may be an enzymatically or metabolically cleavable unit or hydrolysable bond which may be cleaved under enteric and/or gastrointestinal conditions (pH) or other physiological conditions.

In accordance with the present invention, R$_1$ may be selected, for example, from the group consisting of (HO)$_2$P(O) and (MO)$_2$P(O), wherein M is an alkali metal (e.g. Na, K, Cs, etc) or alkaline earth metal (Ca, Mg, etc.).

Further in accordance with the present invention, R$_1$ may be a group of formula R$_{1A}$—CO—, wherein R$_{1A}$ may be selected, for example, from the group consisting of a straight or branched alkyl group of 1 to 6 carbon atoms (e.g. methyl, ethyl, propyl, iso-propyl, butyl, iso-butyl, tert-butyl, tert-butyl-CH$_2$—, etc.), a cycloalkyl group having 3 to 6 carbon atoms (e.g. cyclopropyl-, cyclohexyl- etc.), a cycloalkylalkyl group having 3 to 6 carbon atoms in the cycloalkyl part thereof and 1 to 3 carbon atoms in the alkyl part thereof, (e.g. cyclopropyl-CH$_2$—, cyclohexyl-CH$_2$—, etc.), an alkyloxy group of 1 to 6 carbon atoms (e.g. CH$_3$O—, CH$_3$CH$_2$O—, iso-butylO-, tert-butylO— (Boc), etc.), —CH$_2$OH, CH$_3$O$_2$C—, CH$_3$O$_2$CCH$_2$—, Acetyl-OCH$_2$CH$_2$—, HO$_2$CCH$_2$—, 2-hydroxyphenyl, 3-hydroxyphenyl, 4-hydroxyphenyl, (CH$_3$)$_2$NCH$_2$—, (CH$_3$)$_2$CHCH(NH$_2$)—, HOCH$_2$CH$_2$NH—, CH$_3$OCH$_2$O—, CH$_3$OCH$_2$CH$_2$O—, 2-pyrrolyl, 2-pyridyl, 3-pyridyl, 4-pyridyl, 1-methyl-1,4-dihydro-3-pyridyl, 2-pyrazinyl, 2-quinolyl, 3-quinolyl, 4-quinolyl, 1-isoquinolyl, 3-isoquinolyl, 2-quinoxalinyl, a phenyl group of formula

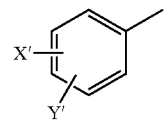

a picolyl group selected from the group consisting of

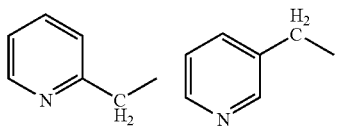

(2-picolyl)    (3-picolyl)    and

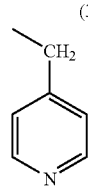

(4-picolyl)

a picolyloxy group selected from the group consisting of

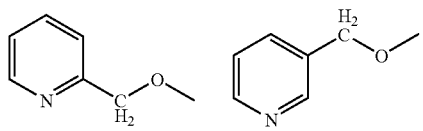

(2-picolyloxy)    (3-picolyloxy)    and

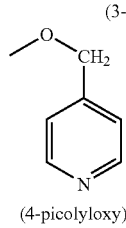

(4-picolyloxy)

a substituted pyridyl group selected from the group consisting of

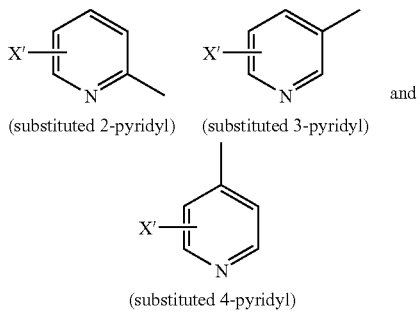

(substituted 2-pyridyl)    (substituted 3-pyridyl)

(substituted 4-pyridyl)

and a group of formula,

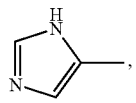

wherein X', Y', $R_4$ and $R_5$ are as defined herein.

The present invention further provides in another aspect a compound of formula II,

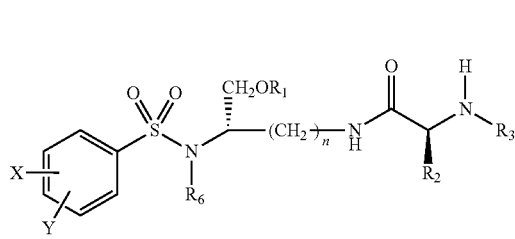

pharmaceutically acceptable salts and derivatives thereof (e.g., for example, when the compound of the present invention comprises an amino group, the pharmaceutically acceptable salt may be an ammonium salt),
wherein n may be 3 or 4,
wherein X and Y, the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_4R_5$, —NHCOR$_4$, —OR$_4$, —SR$_4$, —COOR$_4$, —COR$_4$, and —$CH_2OH$ or X and Y together together define an alkylenedioxy group selected from the group consisting of a methylenedioxy group of formula —$OCH_2O$— and an ethylenedioxy group of formula —$OCH_2CH_2O$—,
wherein $R_6$ may be selected, for example, from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof,
wherein $R_3$ may be selected, for example, from the group consisting of H, a straight alkyl group of 1 to 6 carbon atoms, a branched alkyl group of 3 to 6 carbon atoms, a cycloalkyl group of 3 to 6 carbon atoms, and a group of formula $R_{3A}$—CO—, wherein $R_{3A}$ may be selected, for example, from the group consisting of a straight or branched alkyl group of 1 to 6 carbon atoms (e.g. methyl, ethyl-, propyl, iso-propyl, butyl, iso-butyl, tert-butyl, tert-butyl-$CH_2$—, etc.), a cycloalkyl group having 3 to 6 carbon atoms (e.g. cyclopropyl-, cyclohexyl- etc.), a cycloalkylalkyl group having 3 to 6 carbon atoms in the cycloalkyl part thereof and 1 to 3 carbon atoms in the alkyl part thereof, (e.g. cyclopropyl-$CH_2$—, cyclohexyl-$CH_2$—, etc.), an alkyloxy group of 1 to 6 carbon atoms (e.g. $CH_3O$—, $CH_3CH_2O$—, iso-butylO-, tert-butylO-(Boc), etc.), tetrahydro-3-furanyloxy, —$CH_2OH$, —$CF_3$, —$CH_2CF_3$, —$CH_2CH_2CF_3$, ppyrrolidinyl, piperidinyl, 4-morpholinyl, $CH_3O_2C$—, $CH_3O_2CCH_2$—, Acetyl-$OCH_2CH_2$—, $HO_2CCH_2$—, 3-hydroxyphenyl, 4-hydroxyphenyl, 4-$CH_3OC_6H_4CH_2$—, $CH_3NH$—, $(CH_3)_2N$—, $(CH_3CH_2)_2N$—, $(CH_3CH_2CH_2)_2N$—, $HOCH_2CH_2NH$—, $CH_3OCH_2O$—, $CH_3OCH_2CH_2O$—, $C_6H_5CH_2O$—, 2-pyrrolyl, 2-pyridyl, 3-pyridyl, 4-pyridyl, 2-pyrazinyl, 2-quinolyl, 3-quinolyl, 4-quinolyl, 1-isoquinolyl, 3-isoquinolyl, 2-quinoxalinyl, a phenyl group of formula

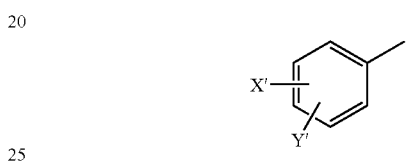

a picolyl group selected from the group consisting of

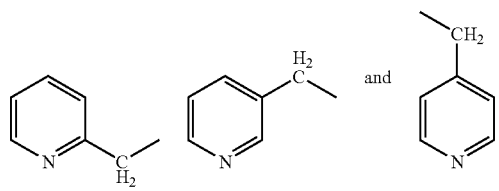

a picolyloxy group selected from the group consisting of

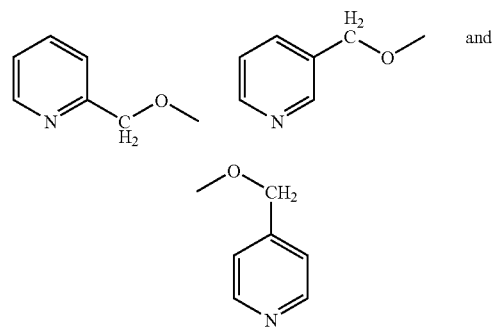

a substituted pyridyl group selected from the group consisting of

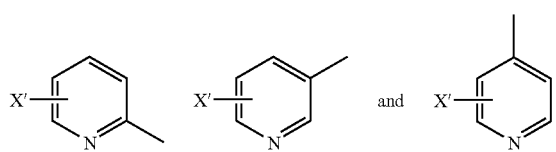

and a group of formula,

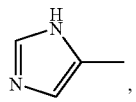

wherein X' and Y', the same or different, may be selected, for example, from the group consisting of H, a straight alkyl group of 1 to 6 carbon atoms, a branched alkyl group of 3 to 6 carbon atoms, a cycloalkcyl group of 3 to 6 carbon atoms, F, Cl, Br, I, —CF$_3$, —NO$_2$, —NR$_4$R$_5$, —NHCOR$_4$, —OR$_4$, —SR$_4$, —COOR$_4$, —COR$_4$ and —CH$_2$OH,
wherein R$_4$ and R$_5$, the same or different, may be selected, for example, from the group consisting of H, a straight alkyl group of 1 to 6 carbon atoms, a branched alkyl group of 3 to 6 carbon atoms, and a cycloalkyl group of 3 to 6 carbon atoms,
wherein R$_2$ may be selected from the group consisting of a diphenylmethyl group of formula IV

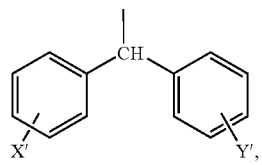

a naphthyl-1-CH$_2$— group of formula V

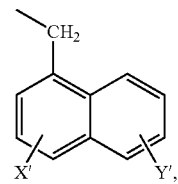

a naphthyl-2-CH$_2$— group of formula VI

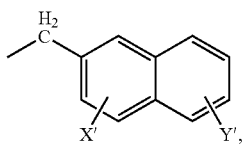

a biphenylmethyl group of formula VII

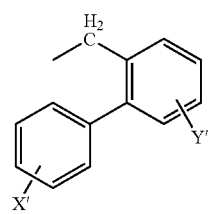

and an anthryl-9-CH$_2$— group of formula VIII

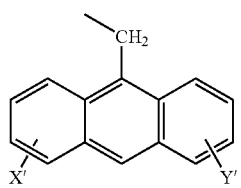

and wherein R$_1$ may be a physiologically cleavable unit, whereby upon cleavage of the unit the compound may be able to release a protease inhibitor, provided that R$_1$ is not H.

In accordance with the present invention, R$_1$ may be selected, for example, from the group consisting of (HO)$_2$P(O) and (MO)$_2$P(O), wherein M is an alkali metal (e.g. Na, K, Cs, etc) or alkaline earth metal (Ca, Mg, etc.).

Further in accordance with the present invention R$_1$ may be a group of formula R$_{1A}$—CO—,
wherein R$_{1A}$ may be selected from the group consisting of a straight or branched alkyl group of 1 to 6 carbon atoms (e.g. methyl, ethyl, propyl, iso-propyl, butyl, iso-butyl, tert-butyl, tert-butyl-CH$_2$—, etc.), a cycloalkyl group having 3 to 6 carbon atoms (e.g. cyclopropyl-, cyclohexyl- etc.), a cycloalkylalkyl group having 3 to 6 carbon atoms in the cycloalkyl part thereof and 1 to 3 carbon atoms in the alkyl part thereof, (e.g. cyclopropyl-CH$_2$—, cyclohexyl-CH$_2$—, etc.), an alkyloxy group of 1 to 6 carbon atoms (e.g. CH$_3$O—, CH$_3$CH$_2$O—, iso-butylO-, tert-butylO— (Boc), etc.), —CH$_2$OH, CH$_3$O$_2$C—, CH$_3$O$_2$CCH$_2$—, Acetyl-OCH$_2$CH$_2$—, HO$_2$CCH$_2$—, 2-hydroxyphenyl, 3-hydroxyphenyl, 4-hydroxyphenyl, (CH$_3$)$_2$NCH$_2$—, (CH$_3$)$_2$CHCH(NH$_2$)—, HOCH$_2$CH$_2$NH—, CH$_3$OCH$_2$O—, CH$_3$OCH$_2$CH$_2$O—, 2-pyrrolyl, 2-pyridyl, 3-pyridyl, 4-pyridyl, 1-methyl-1,4-dihydro-3-pyridyl, 2-pyrazinyl, 2-quinolyl, 3-quinolyl, 4-quinolyl, 1-isoquinolyl, 3-isoquinolyl, 2-quinoxalinyl, a phenyl group of formula

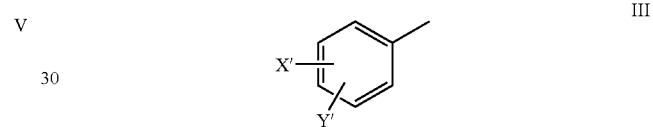

a picolyl group selected from the group consisting of

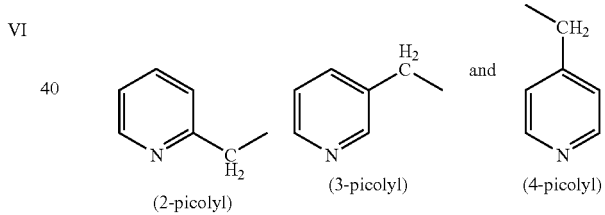

a picolyloxy group selected from the group consisting of

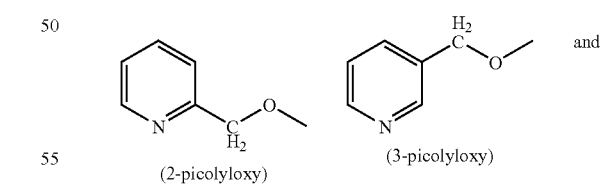

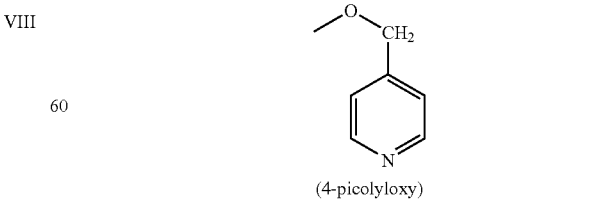

a substituted pyridyl group selected from the group consisting of

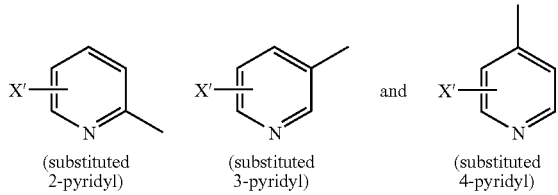

(substituted 2-pyridyl)    (substituted 3-pyridyl)    (substituted 4-pyridyl)

and a group of formula,

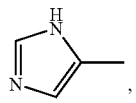

wherein X', Y', $R_4$ and $R_5$ are as defined herein.

In a further aspect, the present invention provides a compound of formula IIa;

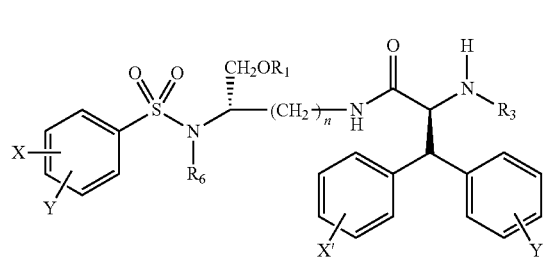

IIa pharmaceutically acceptable salts and derivatives thereof (e.g., for example, when the compound of the present invention comprises an amino group, the pharmaceutically acceptable salt may be an ammonium salt), wherein X and Y, the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_4R_5$, —NHCOR$_4$, —OR$_4$, —SR$_4$, —COOR$_4$, —COR$_4$, and —$CH_2OH$ or X and Y together define an alkylenedioxy group selected from the group consisting of a methylenedioxy group of formula —$OCH_2O$— and an ethylenedioxy group of formula —$OCH_2CH_2O$—, wherein X' and Y', the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_4R_5$, —NHCOR$_4$, —OR$_4$, —SR$_4$, —COOR$_4$, —COR$_4$ and —$CH_2OH$, and wherein n, $R_1$, $R_3$, $R_4$, $R_5$ and $R_6$ are as defined herein.

In an additional aspect, the present invention provides a compound of formula IIb

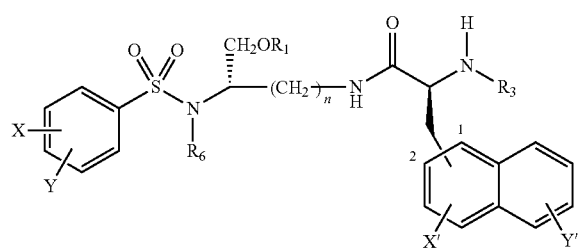

IIb pharmaceutically acceptable salts and derivatives thereof (e.g., for example, when the compound of the present invention comprises an amino group, the pharmaceutically acceptable salt may be an ammonium salt), wherein X and Y, the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_4R_5$, —NHCOR$_4$, —OR$_4$, —SR$_4$, —COOR$_4$, —COR$_4$, and —$CH_2OH$ or X and together define an alkylenedioxy group selected from the group consisting of a methylenedioxy group of formula —$OCH_2O$— and an ethylenedioxy group of formula —$OCH_2CH_2O$—, wherein X' and Y', the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_4R_5$, —NHCOR$_4$, —OR$_4$, —SR$_4$, —COOR$_4$, —COR$_4$ and —$CH_2OH$, and wherein n, $R_1$, $R_3$, $R_4$, $R_5$ and $R_6$ are as defined herein.

In yet an additional aspect, the present invention provides a compound of formula IIc

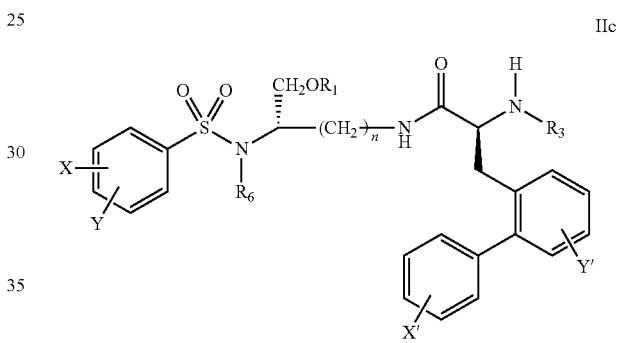

IIc pharmaceutically acceptable salts and derivatives thereof (e.g., for example, when the compound of the present invention comprises an amino group, the pharmaceutically acceptable salt may be an ammonium salt), and wherein n, X, Y, X', Y', $R_1$, $R_3$, $R_4$, $R_5$ and $R_6$ are as defined herein.

In another aspect, the present invention relates to a compound of formula IIA;

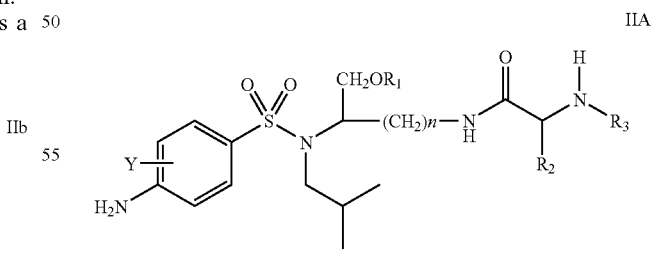

IIA wherein Y, n, $R_1$, $R_2$, $R_3$, X' and Y' are as defined herein. In accordance with the present invention, $R_1$ may be, for example, $(HO)_2P(O)$ or $(NaO)_2P(O)$. Further in accordance with the present invention, n may be 4. Y may be, for example, H. $R_3$ may be, for example, $CH_3O$—CO. $R_2$ may be, for example, a diphenylmethyl group of formula IV, where X' and Y' may be, for example H,

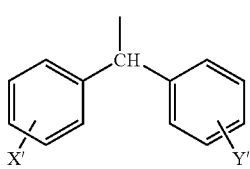

IV

Therefore, compounds of formula IIA' as well as pharmaceutically acceptable salts and derivatives thereof are encompassed by the present invention,

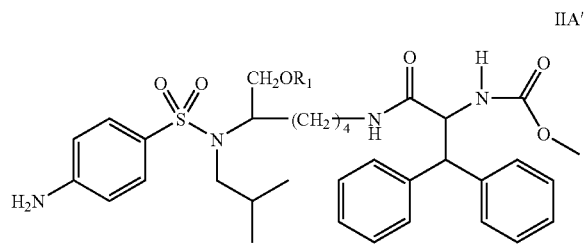

IIA' such as, for example, compound of formula IIA' wherein $R_1$ is $(HO)_2P(O)$ or, compound of formula IIIA' wherein $R_1$ is $(NaO)_2P(O)$.

In yet another aspect, the present invention relates to a pharmaceutical composition comprising at least one compound of formula I, II, IIa, IIb, IIc, IIA, IIIA' or combination of compounds of formula I, II, IIa IIb, IIc, IIA and/or IIA'. The pharmaceutical composition may comprise a pharmaceutically acceptable carrier. The pharmaceutical composition may comprise, for example, a pharmaceutically effective amount of such one or more compounds or as applicable, pharmaceutically acceptable ammonium salts thereof.

For example, pharmaceutical composition of the present invention may comprise one or more of the following compounds;

a compound of formula IIa wherein n is 4, $R_1$ is $(HO)_2P(O)$, X is 4-$NH_2$, Y is H, X' is H, Y' is H, $R_6$ is iso-butyl and $R_3$ is $CH_3O$—CO, a compound of formula IIa wherein n is 4, $R_1$ is $(NaO)_2P(O)$, X is 4-$NH_2$, Y is H, X' is H, Y' is H, $R_6$ is iso-butyl and $R_3$ is $CH_3O$—CO, a compound of formula IIa wherein n is 4, $R_1$ is $(HO)_2P(O)$, X is 4-$NH_2$, Y is H, X' is H, Y' is H, $R_6$ is iso-butyl and $R_3$ is $CH_3CO$, a compound of formula IIa wherein n is 4, $R_1$ is $(HO)_2P(O)$, X is 4-$NH_2$, Y is 3-F, X' is H, Y' is H, $R_6$ is iso-butyl and $R_3$ is $CH_3O$—CO, a compound of formula IIa wherein n is 4, $R_1$ is $CH_3CO$, X is 4-$NH_2$, Y is H, X' is H, Y' is H, $R_6$ is iso-butyl and $R_3$ is $CH_3O$—CO, a compound of formula IIa wherein n is 4, $R_1$ is 3-pyridyl-CO, X is 4-$NH_2$, Y is H, X' is H, Y' is H, $R_6$ is iso-butyl and $R_3$ is $CH_3O$—CO, a compound of formula IIa wherein n is 4, $R_1$ is $(CH_3)_2NCH_2CO$, X is 4-$NH_2$, Y is H, X' is H, Y' is H, $R_6$ is iso-butyl and $R_3$ is $CH_3O$—CO, a compound of formula IIa wherein n is 4, $R_1$ is $(CH_3)_2CHCH(NH_2)CO$, X is 4-$NH_2$, Y is H, X' is H, Y' is H, $R_6$ is iso-butyl and $R_3$ is $CH_3O$—CO, a compound of formula IIb wherein n is 4, $R_1$ is $(HO)_2P(O)$, X is 4-$NH_2$, Y is H, X' is H, Y' is H, $R_6$ is iso-butyl and $R_3$ is $CH_3O$—CO and wherein the naphthyl group is a naphthyl-2-$CH_2$ group, a compound of formula IIb wherein n is 4, $R_1$ is $(HO)_2P(O)$, X is 4-$NH_2$, Y is H, X' is H, Y' is H, $R_6$ is iso-butyl and $R_3$ is 4-morpholine-CO and wherein the naphthyl group is a naphthyl-1-$CH_2$ group, or a combination of any of the above mentioned compounds.

In an additional aspect, the present invention relates to the use of at least one compound of formula I, II, IIa, IIb, IIc, IIA, IIA' or combination of compounds of formula I, II, IIa IIb, IIc, IIA and/or IIA' or pharmaceutically acceptable salts or derivatives thereof (as well as their combinations) in the manufacture of a drug (or pharmaceutical composition) for the treatment or prevention of an HIV infection.

In a further aspect, the present invention relates to the use of at least one compound of formula I, II, IIa, IIb, IIc, IIA, IIA' or combination of compounds of formula I, II, IIa IIb, IIc, IIA and/or IIA' or pharmaceutically acceptable salts or derivatives thereof in the treatment or prevention of an HIV infection in a mammal in need thereof or for delaying the apparition of AIDS.

In yet a further aspect, the present invention relates to a method of treating or preventing an HIV infection (or for delaying the apparition of AIDS) comprising administering at least one compound of formula I, II, IIa, IIb, IIc, IIA, IIA' or combination of compounds of formula I, II, IIa IIb, IIc, IIA and/or IIA' or pharmaceutically acceptable salts or derivatives thereof to a mammal in need thereof.

In another aspect the present invention relates to a compound of formula I, II, IIa, IIb, IIc, IIA or IIA', pharmaceutically acceptable salts or derivatives thereof for use in the treatment or prevention of an HIV infection.

In yet a further aspect the present invention relates to a method of fabricating a lysine based compound using any one of the compounds disclosed in U.S. Pat. No. 6,632,816 to Stranix et al. or a method of fabricating a compound able to generate any one of the disclosed in U.S. Pat. No. 6,632,816 to Stranix et al. upon cleavage of a (in vivo) cleavable unit.

The compounds listed herein are exemplary embodiments of the present invention and it is to be understood that the present invention is not restricted to these compounds only.

The term "pharmaceutically effective amount" refers to an amount effective in treating or preventing HIV infection in a patient or for reducing or eliminating symptoms of AIDS. It is also to be understood herein that a "pharmaceutically effective amount" may be construed as an amount giving a desired therapeutic effect, either taken into a single or multiple doses or in any dosage or route or taken alone or in combination with other therapeutic agents. In the case of the present invention, a "pharmaceutically effective amount" may be understood as an amount having an inhibitory effect on HIV (HIV-1 and HIV-2 as well as related viruses (e.g., HTLV-I and HTLV-II, and simian immunodeficiency virus (SIV))) infection cycle (e.g., inhibition of replication, reinfection, maturation, budding etc.) and on any organism which rely on aspartyl proteases for its life cycle. An inhibitory effect is to be understood herein as an effect such as a reduction in the capacity of an organism (e.g. HIV) to reproduce itself (replicate), to re-infect surrounding cells, etc, or even a complete inhibition (or elimination) of an organism.

The terms "HIV protease" and "HIV aspartyl protease" are used interchangeably and include the aspartyl protease encoded by the human immunodeficiency virus type 1 or 2.

The term "prophylactically effective amount" refers to an amount effective in preventing HIV infection in a patient. As used herein, the term "patient" refers to a mammal, including a human.

The terms "pharmaceutically acceptable carrier", "pharmaceutically acceptable adjuvant" and "physiologically acceptable vehicle" refer to a non-toxic carrier or adjuvant that may be administered to a patient, together with one or more compounds of the present invention, and which does not destroy the pharmacological activity thereof.

The present invention provides pharmaceutically acceptable derivatives of the compounds of formula I (such as compounds of formulae II, IIa, IIb, IIc, IIA and IIA') and where applicable pharmaceutically acceptable salts thereof such as, for example, ammonium salts. A "pharmaceutically acceptable derivative" means any pharmaceutically acceptable salt, ester, or salt of such ester, of a compound of this invention or any other compound which, upon administration to a recipient, is capable of providing (directly or indirectly) a compound of this invention or an antivirally active metabolite or residue thereof.

It is to be understood herein that a "straight alkyl group of 1 to 6 carbon atoms" includes for example, methyl, ethyl, propyl, butyl, pentyl, hexyl.

It is to be understood herein that a "branched alkyl group of 3 to 6 carbon atoms" includes for example, without limitation, iso-butyl, tert-butyl, 2-pentyl, 3-pentyl, etc.

It is to be understood herein, that a "cycloalkyl group having 3 to 6 carbon" includes for example, without limitation, cyclopropyl, cyclobutyl, cyclopentyl, cyclocyclohexyl (i.e., $C_6H_{11}$).

Salts derived from appropriate bases include alkali metal (e.g., sodium), alkaline earth metal (e.g., magnesium), ammonium and N—$(C_{1-4}$ alkyl$)_4^+$ salts.

The compounds of this invention contain one or more asymmetric carbon atoms and thus may occur as racemates and racemic mixtures, single enantiomer, diastereomeric mixtures and individual diastereoisomers. All such isomeric forms of these compounds are expressly included in the present invention. Each stereogenic carbon may be of the R or S configuration.

Pharmaceutically acceptable salts of the compounds of this invention include those derived from pharmaceutically acceptable inorganic and organic acids and bases. Examples of such acid salts include: acetate, adipate, alginate, aspartate, benzoate, benzenesulfonate, bisulfate, butyrate, citrate, camphorate, camphorsulfonate, cyclopentanepropionate, digluconate, dodecylhydrogensulfate, dodecylsulfate, ethanesulfonate, formate, fumarate, glucoheptanoate, glycerophosphate, glycollate, hemisulfate, heptanoate, hexanoate, hydrochloride, hydrobromide, hydroiodide, 2-hydroxyethanesulfonate, lactate, maleate, malonate, methanesulfonate, 2-naphthylsulfonate, nicotinate, nitrate, oxalate, pamoate, pectinate, perchlorate, persulfate, 3-phenylpropionate, phosphate, picrate, pivalate, propionate, salicylate, succinate, sulfate, tartrate, thiocyanate, tosylate, and undecanoate.

This invention also envisions the quaternization of any basic nitrogen containing groups of the compounds disclosed herein. The basic nitrogen may be quaternized with any agents known to those of ordinary skill in the art including, for example, lower alkyl halides, such as methyl, ethyl, propyl and butyl chlorides, bromides and iodides; dialkyl sulfates including dimethyl, diethyl, dibutyl and diamyl sulfates; long chain halides such as decyl, lauryl, myristyl and stearyl chlorides, bromides and iodides, and aralkyl halides including benzyl and phenethyl bromides. Water or oil-soluble or dispersible products may be obtained by such quaternization.

It is to be understood herein, that if a "range" or "group of substances" is mentioned with respect to a particular characteristic (e.g., temperature, concentration, time and the like) of the present invention, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein. Thus, for example, with respect to the number of carbon atoms, the mention of the range of 1 to 6 carbon atoms is to be understood herein as incorporating each and every individual number of carbon atoms as well as sub-ranges such as, for example, 1 carbon atoms, 3 carbon atoms, 4 to 6 carbon atoms, etc.

with respect to reaction time, a time of 1 minute or more is to be understood as specifically incorporating herein each and every individual time, as well as sub-range, above 1 minute, such as for example 1 minute, 3 to 15 minutes, 1 minute to 20 hours, 1 to 3 hours, 16 hours, 3 hours to 20 hours etc.;

and similarly with respect to other parameters such as concentrations, elements, etc. . . .

It is in particular to be understood herein that the compound formulae each include each and every individual compound described thereby as well as each and every possible class or sub-group or sub-class of compounds whether such class or sub-class is defined as positively including particular compounds, as excluding particular compounds or a combination thereof; for example an exclusionary definition for the formula (e.g. I) may read as follows: "provided that when one of A and B is —COOH and the other is H, —COOH may not occupy the 4' position".

It is also to be understood herein that "g" or "gm" is a reference to the gram weight unit and "C", or "° C." is a reference to the Celsius temperature unit.

The compounds of the present invention may easily be prepared using conventional techniques from readily available starting materials. The detailed descriptions of these approaches are presented, for example, in schemes 1 to 5 discussed below.

Scheme 1 illustrates a generic example for the preparation of the phosphate monoester III derived from a primary alcohol (see I), a compound of HIV protease inhibitors (see example 1 (step G and H) in the experimental portion of this document for a specific example of this synthesis).

Note:

a) $R_2$ and $R_3$ are as defined herein.

The synthesis of phosphate monoester III may use a HIV aspartyl protease inhibitor (I, see U.S. Pat. No. 6,632,816) as the starting material. The diethyl phosphotriester II was obtained in good yield upon treatment with diethyl chlorophosphate and sodium hydride in a mixture of tetrahydrofuran and triethylphosphate. Then, addition of trimethysilyl bromide in dichloromethane (DCM) gave compound III in good to excellent yields.

Scheme 1
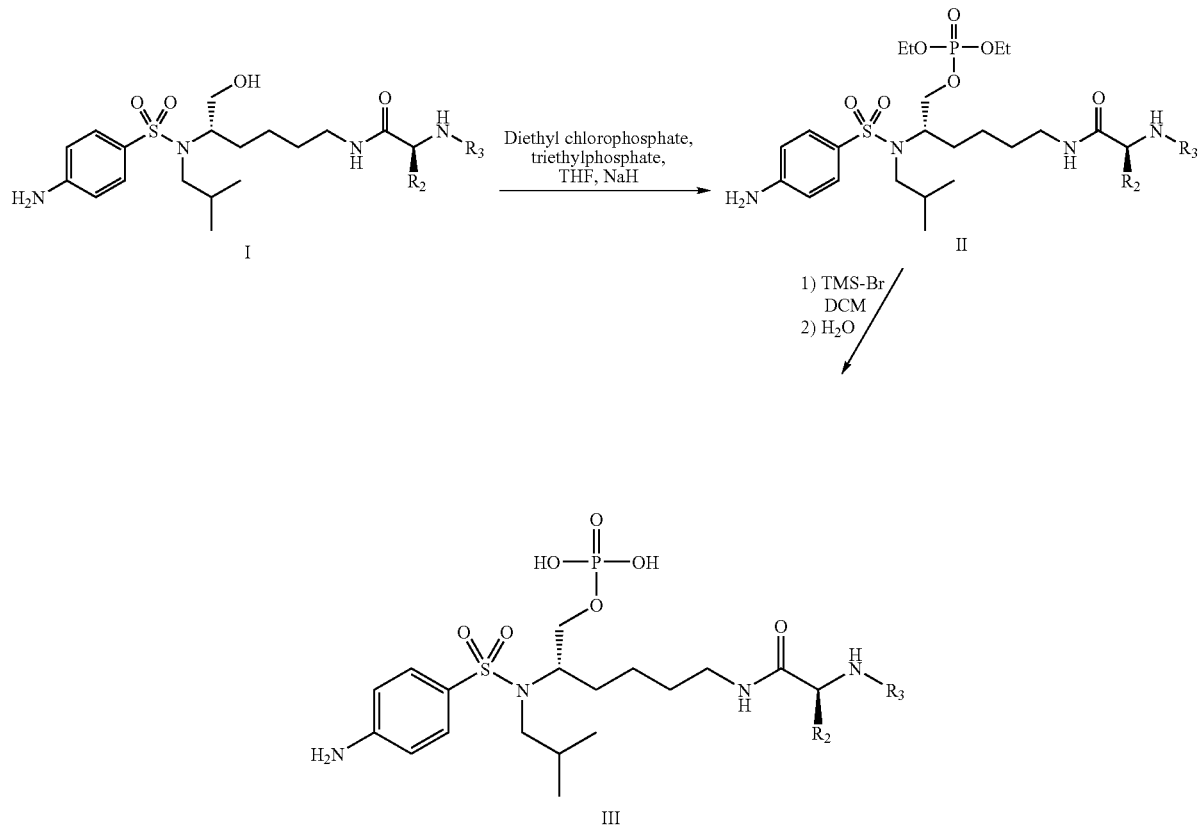
Scheme 1A represents another generic example for the preparation of the phosphate monoester IIIA derived from a primary alcohol (see IA), a compound of HIV protease inhibitors.
Note:
a) n, X, Y, $R_2$, $R_3$ and $R_6$ are as defined herein.
Scheme 1A
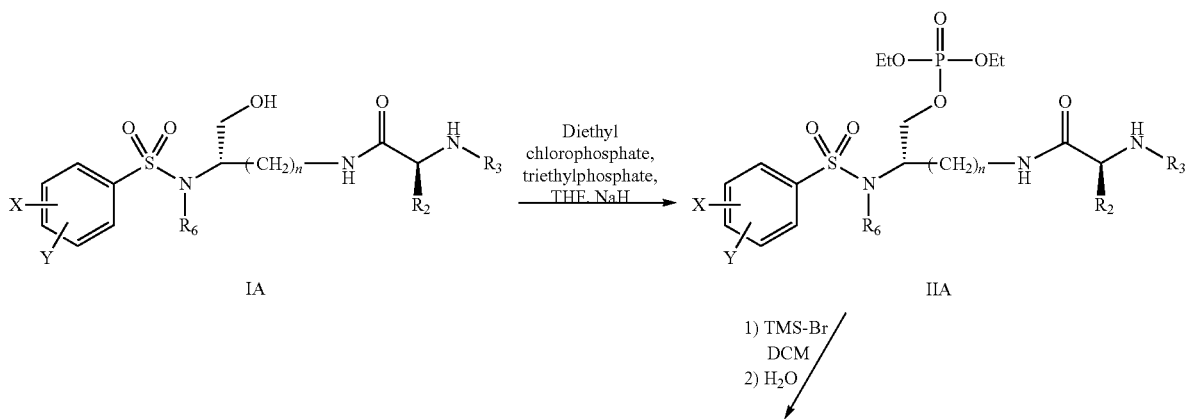

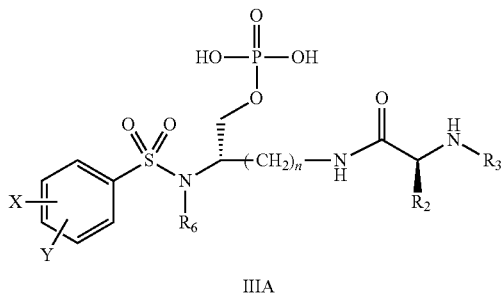

IIIA

The synthesis of phosphate monoester IIIA is performed as described for the preparation of III (scheme 1).

Scheme 2 illustrates a generic example for the preparation of the phosphate monoester III, a compound of HIV protease inhibitors, with a different approach starting from (3S)-3-isobutylamino-azepan-2-one (IV).

Note:
a) $R_2$ and $R_3$ are as defined herein.

As shown in scheme 2, the phosphate monoester derivative III was obtained from (3S)-3-isobutylamino-azepan-2-one (IV) in a seven-step reaction sequence. Initially, (2S)-3-isobutylamino-azepan-2-one (IV) was sulfonated with 4-acetamidobenzenesulfonyl chloride in the presence of triethylamine in dichloromethane to give compound V in excellent yields. The derivative VI was obtained quantitatively upon treatment of V with di-tert-butyl pyrocarbonate and DMAP in acetonitrile. The reductive ring opening with sodium borohydride in ethanol lead to key intermediates VII in good yield. The diethyl phosphotriester VIII was obtained in good yield upon treatment with diethyl chlorophosphate and sodium hydride in a mixture of tetrahydrofuran and triethylphosphate. The Boc protective groups were removed upon treatment with HCl in ethanol to give compound IX quantitatively (T. W. Greene and P. G. M. Wuts, Protective groups in Organic Synthesis, $3^{rd}$ Edition, John Wiley & Sons, Inc. 1999). Then, coupling of the free amino group present on intermediate IX with a variety of synthetic amino acid in the presence of 1-hydroxybenzotriazole (HOBt) and 1-[3-(dimethylamino)propyl]-3-ethylcarbodiimide hydrochloride (EDAC) led to derivative II in good to excellent yields. Finally, addition of trimethysilyl bromide in dichloromethane (DCM) gave compound III in good to excellent yields.

Scheme 2

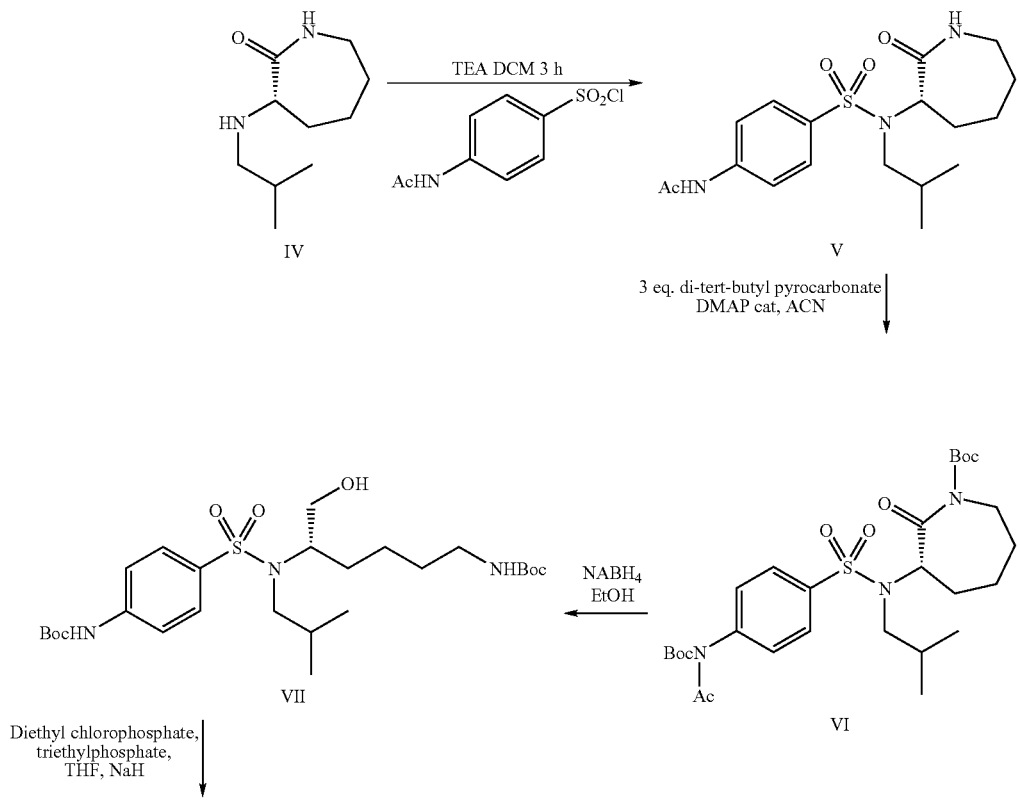

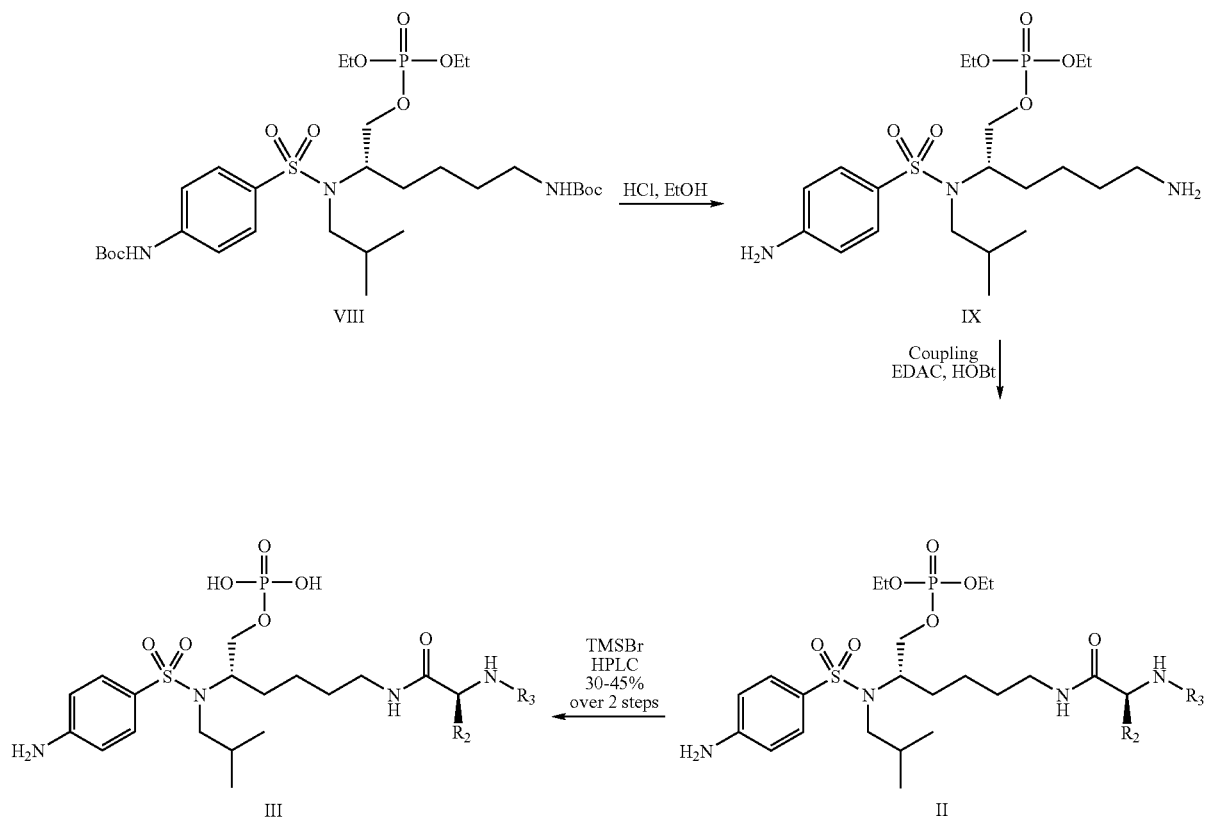

Scheme 3 presents the transformation of a diphenylmethyl derivative; (1S,5S)-(1-{5-[(4-amino-benzenesulfonyl)-isobutyl-amino]-6-hydroxy-hexylcarbamoyl}-2,2-diphenyl-ethyl)-carbamic acid methyl ester (PL-100) into its fluorinated phosphate monoester sodium salt analog XI. This reaction sequence may be used to produce any other similar compounds (compounds) made of unsubstituted (or substituted) diphenylmethyl, 1-naphthyl, 2-naphthyl, biphenyl and 9-anthryl groups described in this invention.

Thus, the treatment of PL-100 with Selectfluor™ in acetonitrile gave derivative X in 38% yield. The introduction of the phosphate monoester group was performed as described previously in scheme 1 and 2. First, the diethyl phosphotriester intermediate was obtained in good yield upon treatment with diethyl chlorophosphate and sodium hydride in a mixture of tetrahydrofuran and triethylphosphate. Secondly, addition of trimethysilyl bromide in dichloromethane (DCM) gave the phosphate monoester compound in good to excellent yields. The final product XI was easily obtained upon treatment of the phosphate monoester with a solution of sodium hydroxide with good yields.

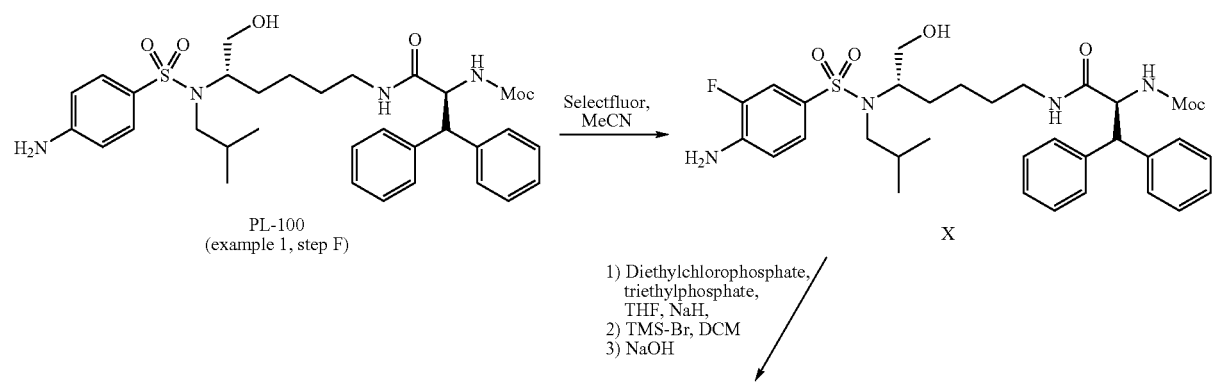

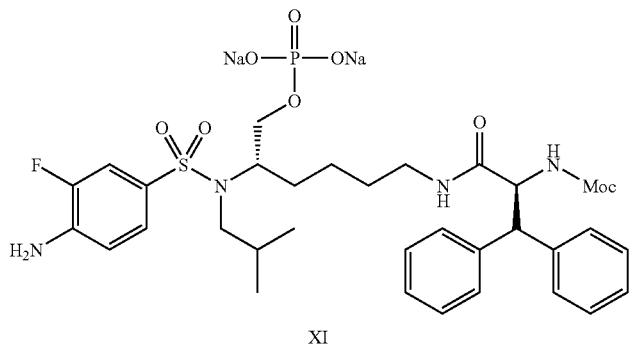

XI

Scheme 4 illustrates a generic example for the transformation of a phosphotriester II into its fluorinated analog XIII in a two-step reaction sequence. This generic example represents a second approach for the synthesis of fluorinated compounds of this invention. In this case, the fluorine atom is added to the phosphotriester II instead of the primary alcohol derivative of general formula I or, more specifically, PL-100 as shown on scheme 3. This alternate reaction sequence may be used to produce any other similar compounds made of unsubstituted (or substituted) diphenylmethyl, 1-naphthyl, 2-naphthyl, biphenyl and 9-anthryl groups described in this invention.

Note:
a) $R_2$ and $R_3$ are as defined herein.

Briefly, treatment of derivative II with Selectfluor™ in acetonitrile gave derivative XII in good yields. Then, addition of trimethysilyl bromide in dichloromethane (DCM) gave the phosphate monoester compound XIII in good to excellent yields. If desired, the final product XIII may be easily transformed into the phosphate monoester sodium salt analog as described before in scheme 3.

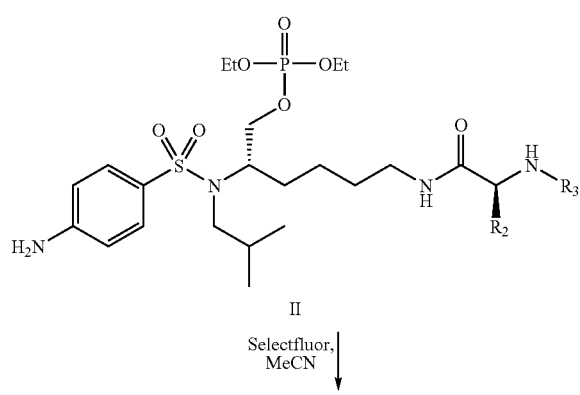

Scheme 4

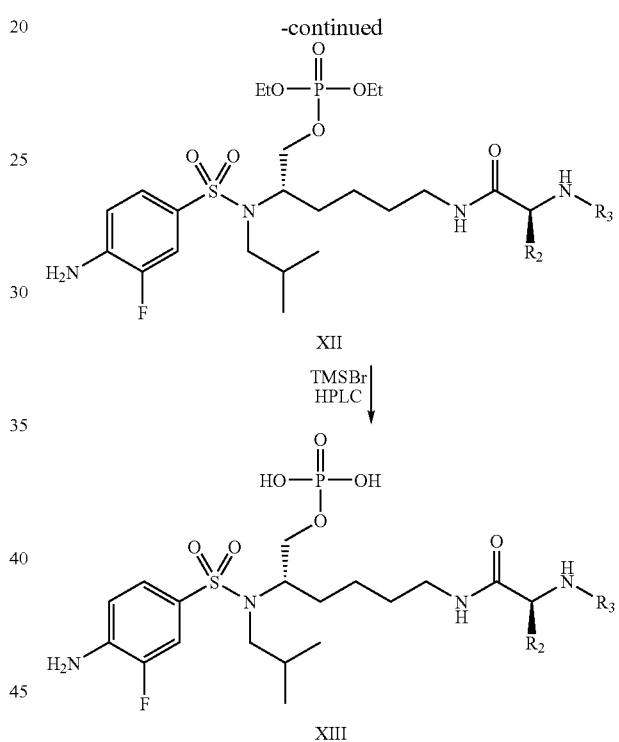

Scheme 5 illustrates the synthesis of various ester compounds XVI in accordance with the invention. The ester compounds are known to be easily cleaved in vivo by esterase enzymes and, as a result, may release the active ingredient. In this scheme $R_2$ is set as a diphenylmethyl group. However, this reaction sequence may be used to produce any other similar compounds made of unsubstituted (or substituted) diphenylmethyl, 1-naphthyl, 2-naphthyl, biphenyl and 9-anthryl groups described in this invention.

Note:
a) $R_{14}$ represents the "residue" of the acid molecule that is linked to the free primary alcohol group present on intermediate XV and is as defined herein.

The compounds XVI are generally obtained in a three-step reaction sequence in high yields. Esterification of (1S)-{4-[(5-tert-butoxycarbonylamino-1-hydroxymethyl-pentyl)-isobutyl-sulfamoyl]-phenyl}-carbamic acid tert-butyl ester (VII) with a variety of acid in the presence of 1-hydroxybenzotriazole (HOBt) and 1-[3-(dimethylamino)propyl]-3-ethylcarbodiimide hydrochloride (EDAC) led to the desired esters XIV in excellent yields. The acetyl ester was obtained quantitatively using acetic anhydride in the presence of N,N-dimethylaminopyridine (DMAP) in dichloromethane (DCM). Cleavage of the Boc protective group was achieved quantitatively upon treatment with trifluoroacetic acid (TFA) in DCM. A second coupling with (2S)-2-methoxycarbonylamino-3,3-diphenyl-propionic acid is performed on the primary amino group of intermediate XV with HOBt and EDAC to give the desired compounds XVI in good to excellent yields. If necessary, catalytic hydrogenation of a benzyloxycarbonyl group is performed using 10% palladium on carbon to give the final compound XVII.

As it may be appreciated by the person skilled in the art, the above synthetic schemes are not intended to be a comprehensive list of all means by which the compound described and claimed in this application may be synthesized but only represent exemplification of synthesis methods among others. Further methods will be evident to those of ordinary skill in the art.

The compounds of this invention may be modified by appending appropriate functionalities to enhance selective biological properties. Such modifications are known in the art and include those which increase biological penetration into a given biological system (e.g., blood, lymphatic system, central nervous system), increase oral availability, increase

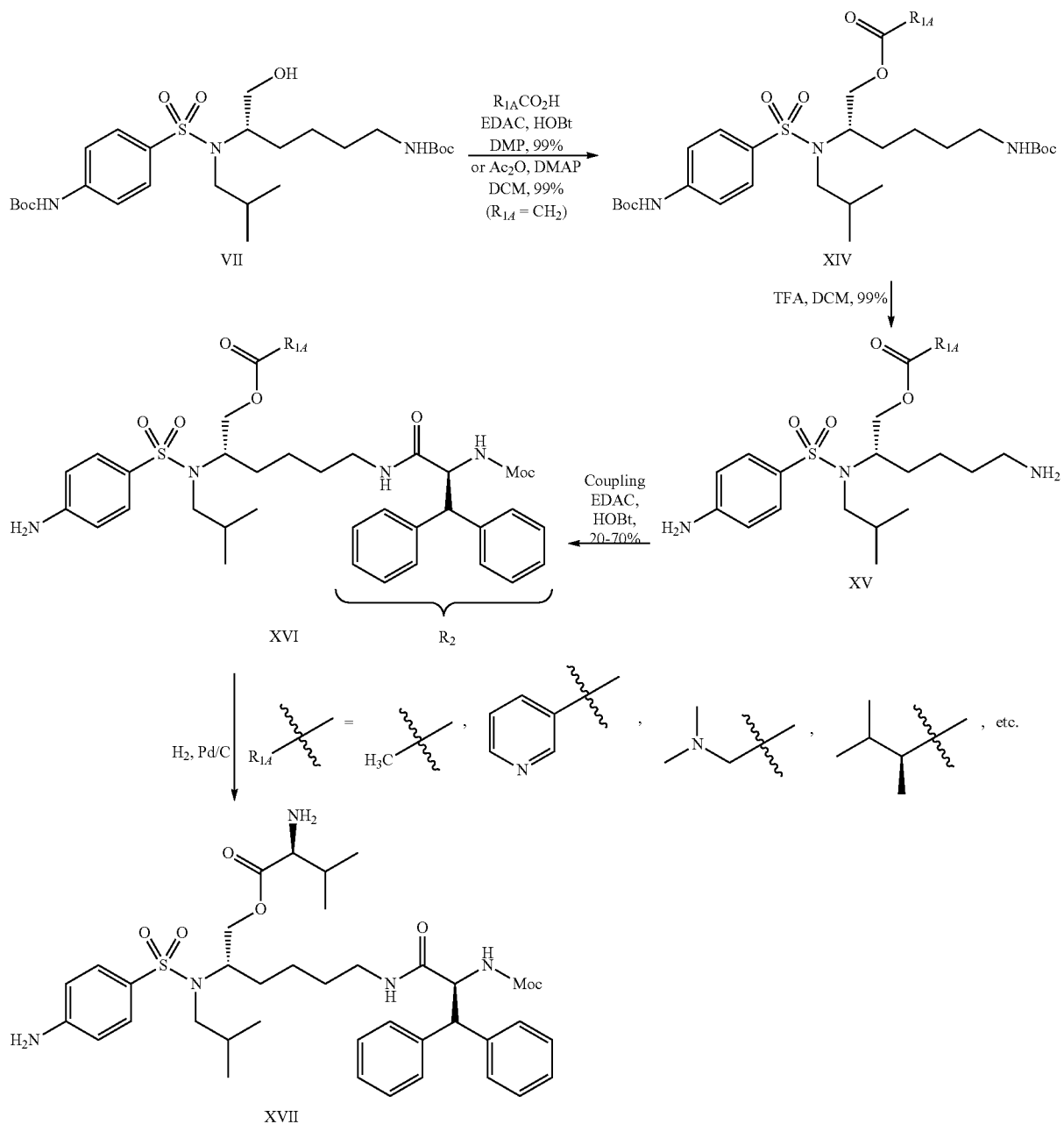

solubility to allow administration by injection, alter metabolism and alter rate of excretion.

As discussed above, the novel compounds may release the active ingredients that are excellent ligands for aspartyl proteases, for example, HIV-1 protease. Accordingly, these compounds are, by releasing the active ingredient, capable of targeting and inhibiting late stage events in the replication, i.e. the processing of the viral polyproteins by HIV encoded protease. Compounds according to this invention advantageously inhibit the ability of the HIV-1 virus to infect immortalized human T cells over a period of days, as determined by an assay measuring the amount of extracellular p24 antigen; a specific marker of viral replication (see, Meek et al., Nature, 343, pp. 90-92 (1990)).

In addition to their use in the prophylaxis or treatment of HIV or HTLV infection, the compounds according to this invention may also be used as inhibitory or interruptive agents for other viruses which use aspartyl proteases, similar to HIV or HTLV aspartyl proteases, in their life cycle. Such compounds inhibit the proteolytic processing of viral polyprotein precursors by inhibiting aspartyl protease. Because aspartyl protease is essential for the production of mature virions, inhibition of that processing effectively blocks the spread of virus by inhibiting the production and reproduction of infectious virions, particularly from acutely and chronically infected cells. The compounds of this invention advantageously inhibit aspartyl proteases, thus blocking the ability of aspartyl proteases to catalyze the hydrolysis of peptide bonds.

The compounds of this invention may be employed in a conventional manner for the treatment or prevention of HIV, HTLV, and other viral infections, which involve a spartyl proteases for their life (replication) cycle. Such methods of treatment, their dosage levels and requirements may be selected by those of ordinary skill in the art from available methods and techniques. For example, a compound of this invention may be combined with a pharmaceutically acceptable adjuvant for administration to a virally infected patient in a pharmaceutically acceptable manner and in an amount effective to lessen the severity of the viral infection.

Alternatively, the compounds of this invention may be used in vaccines and methods for protecting individuals against viral infection over an extended period of time. The compounds may be employed in such vaccines either alone or together with other compounds of this invention in a manner consistent with the conventional utilization of protease inhibitors or protease inhibitors derivatives in vaccines. For example, a compound of this invention may be combined with pharmaceutically acceptable adjuvants, or delivery systems conventionally employed in vaccines and administered in prophylactically effective amounts to protect individuals over an extended period of time against viral infections, such as HIV infection. As such, the novel compounds of the present invention (upon cleavage of a physiologically cleavable unit) may be administered as agents for treating or preventing viral infections, including HIV infection, in a mammal.

The compounds of this invention may be administered to a healthy or HIV-infected patient (before or after the onset of AIDS symptoms) either as a single agent or in combination with other antiviral agents which interfere with the replication cycle of HIV. By administering the compounds of this invention with other antiviral agents which target different events in the viral life cycle, the therapeutic effect of these compounds is potentiated. For instance, the co-administered antiviral agent may be one which targets early events in the viral life cycle, such as attachment to the cell receptor and cell entry, reverse transcription and viral DNA integration into cellular DNA. Antiviral agents targeting such early life cycle events include among others polysulfated polysaccharides, sT4 (soluble CD4) and other compounds which block binding of virus to CD4 receptors on CD4 bearing T-lymphocytes and other CD4(+) cells, or inhibit fusion of the viral envelope with the cytoplasmic membrane, and didanosine (ddI), zalcitabine (ddC), stavudine (d4T), zidovudine (AZT) and lamivudine (3TC) which inhibit reverse transcription. For example another protease inhibitor may be used with compounds of the present invention. Other anti-retroviral and antiviral drugs may also be co-administered with the compounds of this invention to provide therapeutic treatment for substantially reducing or eliminating viral infectivity and the symptoms associated therewith. Examples of other antiviral agents include ganciclovir, dideoxycytidine, trisodium phosphonoformate, eflornithine, ribavirin, acyclovir, alpha interferon and trimenotrexate. Additionally, other types of drugs may be used to potentiate the effect of the compounds of this invention, such as viral uncoating inhibitors, inhibitors of Tat or Rev trans-activating proteins, antisense molecules or inhibitors of the viral integrase. These compounds may also be co-administered with other inhibitors of HIV aspartyl protease. Furthermore, it may be found useful to administer compounds of the present invention with any other drug (other anti-viral compounds, antibiotics, pain killer, etc.,).

Combination therapies according to this invention exert a synergistic effect in inhibiting HIV replication because each component agent of the combination acts on a different site of HIV replication. The use of such combinations also advantageously reduces the dosage of a given conventional anti-retroviral agent that would be required for a desired therapeutic or prophylactic effect as compared to when that agent is administered as a monotherapy. These combinations may reduce or eliminate the side effects of conventional single anti-retroviral agent therapies while not interfering with the anti-retroviral activity of those agents. These combinations reduce the potential of resistance to single agent therapies, while minimizing any associated toxicity. These combinations may also increase the efficacy of the conventional agent without increasing the associated toxicity. Combination therapies encompassed by the present invention include, for example, the administration of a compound of this invention with AZT, 3TC, ddI, ddC, d4T or other reverse transcriptase inhibitors.

Alternatively, the compounds of this invention may also be co-administered with other HIV protease inhibitors such as Ro 31-8959 (Saquinavir; Roche), L-735,524 (Indinavir; Merck), AG-1343 (Nelfinavir; Agouron), A-84538 (Ritonavir; Abbott), ABT-378/r (Lopinavir; Abbott), and VX-478 (Amprenavir; Glaxo) to increase the effect of therapy or prophylaxis against various viral mutants or members of other HIV quasi species.

Administration of compounds of the present invention may be performed, for example, as single agents or in combination with retroviral reverse transcriptase inhibitors, or other HIV aspartyl protease inhibitors. Co-administration of the compounds of this invention with retroviral reverse transcriptase inhibitors or HIV aspartyl protease inhibitors may exert a substantial synergistic effect, thereby preventing, substantially reducing, or completely eliminating viral infectivity and its associated symptoms.

The compounds of the present invention may be administered in such a manner or form which may allow cleavage of the $R_1$ unit to release a protease inhibitor. The compounds of this invention may also be administered, for example, in combination with immunomodulators (e.g., bropirimine, anti-human alpha interferon antibody, IL-2, GM-CSF, methionine enkephalin, interferon alpha, diethyldithiocarbamate sodium, tumor necrosis factor, naltrexone and rEPO) antibiotics (e.g., pentamidine isethionate) or vaccines to prevent or combat infection and disease associated with HIV infection, such as AIDS and ARC.

When the compounds of this invention are administered in combination therapies with other agents, they may be administered sequentially or concurrently to the patient. Alternatively, pharmaceutical or prophylactic compositions according to this invention may be comprised of a combination of one or more compounds of this invention and another therapeutic or prophylactic agent.

Although this invention focuses on the use of the compounds disclosed herein for preventing and treating HIV infection, the compounds of this invention may also be used as inhibitory agents for other viruses that depend on similar aspartyl proteases for obligatory events in their life cycle. These viruses include, but are not limited to, retroviruses causing AIDS-like diseases such as simian imunuodeficiency viruses, HIV-2, HTLV-I and HTLV-II. In addition, the compounds of this invention may also be used to inhibit other aspartyl proteases and, in particular, other human aspartyl proteases including renin and aspartyl proteases that process endothelin precursors.

Pharmaceutical compositions of this invention comprise any of the compounds of the present invention, and pharmaceutically acceptable salts thereof, with any pharmaceutically acceptable carrier, adjuvant, or vehicle. Pharmaceutically acceptable carriers, adjuvants and vehicles that may be used in the pharmaceutical compositions of this invention include, but are not limited to ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethyleneglycol, sodium carboxymethylcellulose, polyacrylates, waxes, polyethylene-polyoxypropylene-block polymers, polyethylene glycol and wool fat.

The pharmaceutical compositions of this invention may be administered orally, parenterally by inhalation spray, topically, rectally, nasally, buccally, vaginally or via an implanted reservoir. It is therefore understood herein that oral administration or administration by injection are encompassed by the present invention. For example, compounds of the present invention, may, for example, be orally administered in an aqueous solution. The pharmaceutical compositions of this invention may contain any conventional non-toxic pharmaceutically acceptable carriers, adjuvants or vehicles. The term "parenteral" as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are amino acid, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in t heir polyoxyethylated versions. These oil solutions or suspensions may also contain a long-chain alcohol diluent or dispersant, such as Ph. Helv or a similar alcohol.

The pharmaceutical compositions of this invention may be orally administered in any orally acceptable dosage form including, but not limited to, capsules, tablets, and aqueous suspension and solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions may be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene or polyoxypropylene compound, emulsifying wax and water. Alternatively, the pharmaceutical compositions may be formulated with a suitable lotion or cream containing the active compound suspended or dissolved in a carrier. Suitable carriers include, but are not limited to, mineral oil, sorbitan monostearate, polysorbate 60, cetyl esters wax cetearyl alcohol, 2-octyldodecanol, benzyl alcohol and water. The pharmaceutical compositions of this invention may also be topically applied to the lower intestinal tract by rectal suppository formulation or in a suitable neat formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline employing benzyl alcohol or other suitable preservatives, absorption promoters to enhance bioavailability, fluorocarbons, and/or other solubilizing or dispersing agents known in the art.

Dosage levels of between about 0.01 and about 25 mg/kg body weight per day, for example form between about 0.5 and about 25 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration may be used as a chronic or acute therapy. The amount of active ingredient that may be combined with the carrier materials to produce a single dosage form will vary depending upon the patient treated and the particular mode of administration. A typical preparation will contain from about 5% to about 95% active compound (w/w). For example, such preparations may contain from about 20% to about 80% active compound.

Upon improvement of a patient's condition, a maintenance dose of a compound, composition or combination of this invention may be administered if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis, upon any recurrence of disease symptoms.

As the person skilled in the art will appreciate, lower or higher doses than those recited above may be desired. Specific dosage and treatment regimen for any particular patient may depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

In the description-herein, the following abbreviations are used:
Abbreviation Meaning
Ac Acetyl
AcOH Acetic acid
APCI Atmospheric pressure chemical ionization
AIDS Acquired Immunodeficiency Syndrome
AZT 3-Azido-3-deoxythymine (Zidovudine)
Boc Benzyloxycarbonyl
t-Butyl tert-Butyl
CAM Cerium ammonium molybdate
DCM Dichloromethane
DMAP N,N-dimethylaminopyridine
DMSO Dimethylsulfoxide
DMF Dimethylformamide
DNA Deoxyribonucleic acid
EDAC 1-[3-(dimethylamino)propyl]-3-ethylcarbodiimide hydrochloride
EtOAc Ethyl acetate
EtOH Ethyl alcohol
g Gram
h hour
HIV-1, -2 Human immunodeficiency virus type 1, type 2
HOBt 1-Hydroxybenzotriazole
HPLC High performance liquid chromatography
HTLV-I, -II Human T-cell lymphotropic virus type I, type II
IL-2 Interleukin-2
Kg Kilogram
L Liter
LC-MS Liquid chromatography-mass spectrometry
M Molar
MeOH Methyl alcohol
mg Milligram
mp Melting point
min Minute
Moc Methoxycarbonyl
mol Mole
mL Milliliter
mmol Millimole
nm Nanometer
nM Nanomolar
po Orally
rEPO Recombinant erythropoietin
TLC Thin layer chromatography
3TC 2',3'-Dideoxy-3-thiacytidine
TFA Trifluoroacetic acid
THF Tetrahydrofuran

EXAMPLES

This section describes the synthesis of lysine based compounds able to release an HIV aspartyl protease inhibitors as described herein. These examples are for the purpose of illustration only and are not to be construed as limiting the scope of the invention in any way. This section presents the detailed synthesis of compounds no. 1 to 10 of this invention.

Materials and Methods

Analytical thin layer chromatography (TLC) was carried out with 0.25 mm silica gel E. Merck 60 $F_{254}$ plates and eluted with the indicated solvent systems. Preparative chromatography was performed by flash chromatography, using silica gel 60 (EM Science) with the indicated solvent systems and positive air pressure to allow proper rate of elution. Detection of the compounds was carried out by exposing eluted plates (analytical or preparative) to iodine, UV light and/or treating analytical plates with a 2% solution of p-anisaldehyde in ethanol containing 3% sulfuric acid and 1% acetic acid followed by heating. Alternatively, analytical plates may be treated with a 0.3% ninhydrin solution in ethanol containing 3% acetic acid and/or a C AM solution made of 20 g $(NH_4)_6Mo_7O_{24}$ and 8.3 g $Ce(SO_4)_2$ polyhydrate in water (750 mL) containing concentrated sulfuric acid (90 mL).

Preparative HPLC were performed on a Gilson apparatus equipped with a C18 column, a 215 liquid handler module and 25 mL/min capacity head pumps. The HPLC is operated with a Gilson UniPoint System Software.

Semi-Preparative HPLC Conditions for Purification of Test Compounds:

HPLC system: 2 Gilson #305-25 mL pumps, Gilson #215 liquid handler for injection and collection and a Gilson #155 UV-Vis absorbance detector, all controlled from a Gilson Unipoint V 1.91 software Column: Alltech (#96053) Hyperprep PEP, C-18, 100 Åα, 8 μm, 22×250 mm Flow: 15 mL/min Solvents: A: $H_2O$; B: $CH_3CN$ Gradient: 25% to 80% of B over 40 min Detector: absorbance; λ: 210 & 265 nm The crude material dissolved in acetonitrile to a concentration of around 50 to 80 mg/2 mL were injected in each run. Fractions were collected in amounts of 9 mL pertaining absorbance was detected at the UV detector.

Unless otherwise indicated, all starting materials were purchased from a commercial source such as Aldrich Co. or Sigma Co.

Melting points (mp) were determined on a Büch 530 melting point apparatus in capillary tubes and were uncorrected.

Mass spectra were recorded on a Hewlett Packard LC/MSD 1100 system using APCI or electrospray sources either in negative mode or positive mode.

Nuclear magnetic resonance (NMR) spectra were recorded on a Bruker AMX-II-500 equipped with a reversed or QNP probe. Samples were dissolved in deuterochloroform ($CDCl_3$), deuteroacetone (acetone-$d_6$), deuteromethanol ($CD_3OD$) or deuterodimethylsulfoxide (DMSO-$d_6$) for data acquisition using tetramethylsilane as internal standard. Chemical shifts (*) are expressed in parts per million (ppm), the coupling constants (J) are expressed in hertz (Hz) whereas multiplicities are denoted as s for singlet, d for doublet, 2d for two doublets, dd for doublet of doublets, t for triplet, q for quartet, quint for quintet, m for multiplet, and br s for broad singlet.

DETAILED DESCRIPTION OF THE INVENTION

Examples

Specific Examples for the Preparation of Derivatives of General Formula I

The following compounds were prepared from L-lysine derivatives using the procedures summarized in schemes 1, 1A, 2, 3, 4 and 5 of this invention.

Example 1

Preparation of (1S,5S)-(1-{5-[(4-amino-benzene-sulfonyl)-isobutyl-amino]-6-phosphonooxy-hexyl-carbamoyl}-2,2-diphenyl-ethyl)-carbamic acid methyl ester (PL-461)

The preparation of the title compound is based on schemes 1 and 2 of this invention.

Step A. Preparation of (3S)-3-isobutylamino-azepan-2-one (IV)

L-α-amino-,-caprolactam (22.0 g) was dissolved in cold dichloroethane (DCM, 200 mL) isobutyraldehyde (12.6 g) was added slowly and stirred until the heat evolved was dissipated (water forms at the surface). The cold solution was added to 46.5 g of powdered $NaBH(OAc)_3$ in DCM (0.5 L). AcOH (70 mL) was added to the solution. The slightly turbid mixture was stirred at 20° C. for 4 h. A 500 mL solution of 2M NaOH was added slowly to the turbid mixture and the pH adjust to 11 using a concentrated NaOH solution, and then the mixture stirred for a further 20 min. After extraction, the DCM layer was dried with $MgSO_4$, filtered and evaporated. The oil thus obtained crystallizes slowly on standing (27.8 g, 85%) and was used without further purification in the next step.

$^1$H NMR ($CDCl_3$): δ 0.93 (d, J=6.5, 3H), 0.97 (d, J=6.5, 3H), 1.39 (t, J=9.8, 1H), 1.47 (m, 1H), 1.78-1.65 (m, 2H), 2.00-1.93 (m, 2H), 2.32-2.2 (m, 2H), 2.38 (t, J=9.7, 1H), 3.16 (m, 3H), 6.62 (s, 1H(NH)). mp 52-54° C. (hexanes).

A small sample was converted to the S-methyl benzyl urea by adding the solid to a solution of S-methyl benzyl isocyanate in MeCN. NMR gives 98% ee Step B. Preparation of Nα-isobutyl-Nα-(4-acetamidobenzenesulfonyl)-L-α-amino-,-caprolactam (V)

Nα-isobutyl-L-α-amino-,-caprolactam (IV) (4.1 g free base) was dissolved in DCM (200 mL) and treated with 4.0 g triethylamine, followed by 4-acetamidobenzenesulfonyl chloride (5.2 g). A 0.1 g portion of dimethylaminopyridine was added and the mixture was stirred 5 h. The resulting thick slurry was poured into 500 mL 0.5 M HCl and shaken vigorously. The solid in the biphasic solution was filtered out and washed with cold acetone to give 7.3 g (87%) of clean product.

$^1$H NMR (DMSO-$d_6$): * 0.93 (d, J=6.0, 3H), 0.96 (d, J=6.0, 3H), 1.39 (t, J=12.0, 1H), 1.85-1.65 (m, 3H), 2.08-2.18 (m and s, 6H), 2.90-2.97 (m, 1H), 3.00-3.06 (m, 2H), 3.35 (dd, J=14.2, 8.5, 1H), 4.65 (d, J=8.7, 1H), 6.3 (s, 1H), 7.42 (d, J=8.8, 2H), 7.6 (d, J=8.8, 2H). mp 230-233° C. (EtOH).

Step C. Preparation of (3S)-3-{[4-(acetyl-tert-butoxycarbonyl-amino)-benzenesulfonyl]-isobutyl-amino}-2-oxo-azepane-1-carboxylic acid tert-butyl ester (Boc activation) (VI)

4.2 g of Nα-isobutyl-Nα-(4-acetamidobenzenesulfonyl)-L-α-amino-,-caprolactam (V) was suspended in 30 mL MeCN and briefly sonicated to break up any large chunks. To this white suspension was added 6.7 g (3 eq.) of di-tert-butyl pyrocarbonate in 10 mL MeCN. The suspension was stirred with a magnetic bar and a 120 mg portion of DMAP was added. The solution becomes a clear light yellow after a few minutes. TLC (EtOAc) reveals 1 product Rf 0.9 (starting material Rf at 0.4). The solution is poured in distilled water 20 mL and extracted with ether, dried with $Na_2SO_4$ and evaporated yielding 6.90 g. A sample was recrystallized from hexanes.

$^1$H NMR (DMSO-$d_6$): * 0.68 (d, J=6.0, 3H), 0.85 (d, J=6.0, 3H), 1.39 (s, 10H), 1.47 (s, 9H), 1.85-1.65 (m, 3H), 2.15 (s, 3H), 2.80 (q, J=4, 1H), 3.10-3.36 (m, 2H), 4.01 (d, J=8.0, 1H), 4.85 (d, J=8.7, 1H), 7.32 (d, J=8.8, 2H), 7.87 (d, J=8.8, 2H). mp 123-124° C.

Step D. Preparation of (1S)-4-amino-N-(5-amino-1-hydroxymethyl-pentyl)-N-isobutyl-benzenesulfonamide (VII-deprotected) (Reductive Ring Opening and Deprotection)

A 3.0 g portion of (3S)-3-{[4-(acetyl-tert-butoxycarbonyl-amino)-benzenesulfonyl]-isobutyl-amino}-2-oxo-azepane-1-carboxylic acid tert-butyl ester (VI, step C) is dissolved in 40 mL EtOH followed by 750 mg $NaBH_4$. Brief heating with a heat gun gives a clear solution. TLC reveals one streaky spot after 20 min (EtOAc). The solution is concentrated to a paste, poured in 40 mL 1N NaOH and extracted with ethyl acetate, the organic phase dried with $NaSO_4$ and evaporated to give 2.8 g of product intermediate (VII); (1S)-{4-[(5-tert-butoxycarbonylamino-1-hydroxymethyl-pentyl)-isobutyl-sulfamoyl]-phenyl}-carbamic acid tert-butyl ester (VII).

The above product intermediate is dissolved in 5 mL EtOH and 5 mL 12 N HCl is added. Vigorous gas evolution is observed for a few minutes. After 2 h the solution is evaporated and rendered basic with concentrated KOH and extracted with EtOAc yielding 1.75 g of a white powder.

$^1$H NMR (DMSO-$d_6$): * 0.82 (m, 6H), 0.97-1.12 (m, 2H), 1.15-1.30 (m, 3H), 1.57 (m, 1H), 1.84 (m, 1H), 2.40 (t, J=7.8, 2H), 2.75 (m, 1H), 2.85 (m, 1H), 3.21 (m, 1H), 3.44 (d, J=6.4, 2H), 5.92 (br s, 2H), 6.59 (d, J=8.0, 2H), 7.39 (d, J=8.0, 2H).

Step E. Preparation (2S)-2-methoxycarbonylamino-3,3-diphenyl-propionic acid

To a solution of L-diphenylalanine (241 mg, 1.0 mmol) Peptech Corp.) in 5 mL 1N NaOH and 0.5 mL saturated $Na_2CO_3$ (resulting solution at pH 10) was added methoxycarbonyloxysuccinimide (carbonic acid 2,5-dioxo-pyrrolidin-1-yl ester methyl ester) (180 mg, 1.1 mmol) dissolved in 5 mL. Afterwards, the reaction mixture was stirred at room temperature for 2 h. The alkaline solution was extracted once with ether (10 mL) and the aqueous phase was acidified with 1N HCl. This was extracted twice with 20 mL EtOAc, and the combined organic phases were washed with 50 mL 1N HCl. The organic phase was dried over $Na_2SO_4$, filtered and evaporated to an oil, which solidifies to yields 250 mg (83%) of the desired material. This derivative was used as such in the next step.

Step F. Preparation of (1S,5S)-(1-{5-[(4-amino-benzenesulfonyl)-isobutyl-amino]-6-hydroxy-hexylcarbamoyl}-2,2-diphenyl-ethyl)-carbamic acid methyl ester (PL-100)

The title compound was prepared from (1S)-4-amino-N-(5-amino-1-hydroxymethyl-pentyl)-N-isobutyl-benzenesulfonamide (VII-deprotected) (step D) and (2S)-2-methoxycarbonylamino-3,3-diphenyl-propionic acid (step E) using the coupling procedure with HOBt and EDAC described in example 3 (step D). The final product was obtained in 67% yield (121 mg).

LC-MS: 625.3 (M+H)$^+$, 95% pure $^1$H NMR (CD$_3$OD): δ 0.71-0.85 (m, 2H), 0.88 (d, J=6.3, 5H), 0.91-0.96 (m, 2H), 1.29-1.34 (m, 1H), 1.41-1.52 (m, 1H) 1.82-1.92 (m, 1H), 2.61-2.68 (m, 1H), 2.81-2.85 (m, 2H), 2.94-3.05 (m, 2H), 3.38-3.40 (t, J=5.0, 1H), 3.50-3.51 (m, 1H), 3.52 (s, 3H), 4.28 (d, J=11.0 1H), 4.87 (d, J=11.0, 1H), 6.69 (d, J=8.0, 2H), 7.15-718 (m, 2H), 7.20-7.31 (m, 6H), 7.33 (d, J=7.9, 2H), 7.47 (d, J=7.5, 1H).

$^{13}$C NMR (CD$_3$OD): δ 20.0, 20.1, 23.3, 25.4, 28.1, 28.5, 28.9, 38.1, 40.0, 51.2, 51.6, 53.1, 57.2, 57.4, 59.5, 61.9, 62.4, 112.6, 125.7, 126.2, 126.3, 127.9, 128.1, 128.15, 128.2, 128.4, 128.7, 141.3, 141.9, 152.4, 155.9, 169.9, 172.5.

Step G. Preparation of (1S,5S)-{1-[5-[(4-aminobenzenesulfonyl)-isobutyl-amino]-6-(diethoxy-phosphoryloxy)-hexylcarbamoyl]-2,2-diphenyl-ethyl}-carbamic acid methyl ester The PL-100 compound (product of step F, 203 mg, 0.325 mmol) was dissolved in dry tetrahydrofuran (3 mL) and 0.2 mL triethylphosphate under N$_2$ atmosphere. The mixture was stirred at this temperature for 15 min, followed by the addition of diethyl chlorophosphate (0.061 mL, 0.423 mmol). Sodium hydride (60% in mineral oil) (17 mg, 0.423 mmol) was added at 0° C. The solution was stirred for 1 h at 0° C. and 12 h at room temperature. 20 mL of Amberlite XAD-2 was added to the solution and the beads were thoroughly mixed with the solvent. To the mixture was added ice water 2 mL, and the THF evaporated off. The beads were then washed with distilled water 6 times 100 mL then extracted three times with ethyl acetate (30 mL). The combined phase was evaporated and the residue was dried under high vacuum. The crude product was purified by flash chromatography using ethyl acetate/hexane (8/2), then EtOAc 100% as eluent. The yield of this reaction is 152 mg 61%.

LC-MS: 761.2 (M+H)$^+$, 90% pure $^1$H NMR (CD$_3$OD): δ 0.68-0.75 (m, 1H), 0.75-0.84 (m, 1H), 0.84-1.10 (m, 9H), 1.21-1.50 (m, 8H), 1.88 (m, 1H), 2.58-2.71 (m, 1H), 2.80-2.89 (m, 1H), 2.89-3.08 (m, 2H), 3.49-3.60 (s, 3H), 3.65-3.74 (m, 1H), 3.85-3.95 (m, 1H), 3.97-4.02 (m, 1H), 4.07-4.21 (m, 4H), 4.29 (d, J=10.8, 1H), 6.71 (d, J=8.0, 2H), 7.10-7.20 (m, 2H), 7.20-7.32 (m, 5H), 7.32-7.45 (m, 3H), 7.50 (d, J=7.5, 2H), 7.86 (br s, 1H).

$^{31}$P NMR (CD$_3$OD): δ 1.62

Step H. Preparation of (1S,5S)-(1-{5-[(4-aminobenzenesulfonyl)-isobutyl-amino]-6-phosphonooxyhexylcarbamoyl}-2,2-diphenyl-ethyl)-carbamic acid methyl ester (PL-461)

The product of step G prepared above (152 mg) was dissolved in anhydrous dichloromethane (3.0 mL). Trimethylsilyl bromide (0.5 mL) was added at 0° C. The mixture was stirred during 1 h at this temperature and overnight at room temperature. The solvent was evaporated and 0.2 mL water was added to the residue. 3 mL EtOH was added mixed and evaporated. This step was repeated three times and the residue dried in vacuo. Yields 98 mg 70% of the title derivatives of this first example.

LC-MS: 705.2 (M+H)$^+$, 95% pure $^1$H NMR (CD$_3$OD): δ 0.65-0.73 (m, 1H), 0.75-0.83 (m, 1H), 0.89 (d, J=5.6, 8H), 1.27-1.38, (m, 1H), 1.42-4.55 (m, 1H), 1.82-1.94 (m, 1H), 2.57-2.68 (m, 1H), 2.78-2.90 (m, 1H), 2.91-3.09 (m, 2H), 3.54 (s, 3H), 3.60-3.72 (m, 1H), 3.87-4.05 (m, 1H), 4.00 (m, 1H), 4.29 (d, J=11.3, 1H), 4.90 (d, J=11.4, 1H), 6.73 (d, J=8.0, 2H), 7.13-7.22 (m, 2H), 7.22-7.33 (m, 6H), 7.33-7.45 (m, 2H), 7.51 (d, J=7.5, 2H). $^{31}$P NMR (CD$_3$OD): δ 2.80

Example 2

Preparation of (1S,5S)-(1-{5-[(4-amino-benzenesulfonyl)-isobutyl-amino]-6-phosphonooxy-hexylcarbamoyl}-2,2-diphenyl-ethyl)-carbamic acid methyl ester sodium salt (PL-462)

70.7 mg of the final product of example 1 is added to 1 mL 0.1 N NaOH and diluted with 1 mL of distilled water. The Solution is then frozen and lyophilized. Yields 67.2 mg (92%) of the desired material with 95% purity.

$^1$H NMR (CD$_3$OD): δ 0.72-0.83 (m, 1H), 0.90 (d, J=5.8, 9H), 1.26-1.38 (m, 1H), 1.53-1.65 (m, 1H), 1.88-2.00 (m, 1H), 2.60-2.70 (m, 1H), 2.79-2.89 (m, 1H), 2.98-3.00 (m, 1H), 3.00-3.08 (m, 1H), 3.54 (s, 3H), 3.58-3.71 (m, 1H), 3.72-3.83 (m, 1H), 3.84-3.95 (m, 1H), 4.28 (d, J=11.1, 1H), 4.91 (d, J=11.0, 1H), 6.70 (d, J=7.6, 2H), 7.12-7.22 (m, 2H), 7.22-7.32 (m, 6H), 7.33-7.40 (m, 2H), 7.50 (d, J=7.7, 2H). $^{31}$P NMR (CD$_3$OD): δ 3.13

Example 3

Preparation of (1S,5S)-(1-{5-[(4-amino-benzenesulfonyl)-isobutyl-amino]-6-phosphonooxy-hexylcarbamoyl}-2-naphthalen-2-yl-ethyl)-carbamic acid methyl ester (PL-507)

The preparation of the title compound is based on scheme 2 of this invention.

Step A. Preparation of (1S)-(4-{[5-tert-butoxycarbonylamino-1-(diethoxyphosphoryloxymethyl)-pentyl]-isobutyl-sulfamoyl}-phenyl)-carbamic acid tert-butyl ester (VIII)

2.00 g (3.7 mmol) (1S)-{4-[(5-tert-butoxycarbonylamino-1-hydroxymethyl-pentyl)-isobutyl-sulfamoyl]-phenyl}-carbamic acid tert-butyl ester (VII) (example 1, step D) is dissolved in 0.63 mL triethylphosphate and 10 mL THF at 0° C. under inert argon atmosphere. 0.63 mL (4.44 mmol) diethylchlorophosphate is added and then 0.25 g (6.2 mmol), NaH 60% in oil is added in portionwise. The mixture is allowed to warm to room temperature and left to stir for 2 h (LC-MS showed completion after 1 h). To the solution is added 20 mL of Amberlite XAD-2 resin and the slurry thoroughly mixed and added to 200 mL ice water. After stirring for 15 min. the resin suspension is filtered and the resin washed several times with distilled water (500 mL). The desired product is desorbed from the resin with acetone (5×50 mL), EtOAc (5×50 mL), the organic phase is then dried over Na$_2$SO$_4$. After evaporation of the solvent 2.66 g (89%) of clear oil is obtained. The crude product contains a fraction with two diethyl phosphates and is used as is in the next step.

$^1$H NMR (CD$_3$OD): δ 0.91 (d, J=6.3, 6H), 1.11-1.21 (m, 2H), 1.33 (t, J=6.9, 10H), 1.43 (s, 9H), 1.53 (s, 10H), 1.90-1.97 (m, 1H), 2.88-2.96 (m, 3H), 2.96-3.04 (m, 1H), 3.81-3.90 (m, 1H), 3.91-3.99 (m, 1H), 4.01-4.14 (m, 4H), 7.61 (d, J=8.3, 2H), 7.72 (d, J=8.4, 2H). $^{31}$P NMR (CD$_3$OD): δ 1.59

Step B. Preparation of (2S)-phosphoric acid 6-amino-2-[(4-amino-benzenesulfonyl)-isobutyl-amino]-hexyl ester diethyl ester (IX)

The crude product obtained in the previous step (VIII, 2.66 g) is dissolved in 12 mL EtOH. 4 mL of HCl is added and heated briefly to 70° C. then left at room temperature for 3 h. The solvent is evacuated and the residue triturated with 50 mL ether. The thick residue is then dissolved in 3 mL ice water and the pH adjusted to 12 with 50% NaOH. The thick slurry obtained is extracted with EtOAc (3×50 mL) and the organic phase dried over Na$_2$SO$_4$. After filtration of the drying agent the organic phase is evacuated to yield 1.84 g (98%) of the desired product (IX).

LC-MS: 480.2 (M+H)$^+$, 95% pure.

$^1$H NMR (CD$_3$OD): δ 0.91 (s, 6H), 1.11-1.26 (m, 3H), 1.28-1.43 (m, 8H), 1.45-1.51 (m, 1H), 1.52-1.61 (m, 1H), 1.89-1.96 (m, 1H), 2.56 (t, J=6.7, 2H), 2.85-2.91 (m, 1H), 2.98-3.11 (m, 1H), 3.79-3.99 (m, 1H), 3.94 (d, J=5.3, 1H), 4.09-4.11 (m, 4H), 6.69 (d, J=7.9, 2H), 7.50 (d, J=7.9, 2H). $^{31}$P NMR (CD$_3$OD): δ 1.61

Step C. Preparation of (2S)-2-methoxycarbonylamino-3-naphthalen-2-yl-propionic acid (or L-Moc-2-naphthylalanine)

To a solution of L-2-naphthylalanine (215 mg, 1 mmol) (Peptech Corp.) in 5 mL 1N NaOH and 0.5 mL saturated Na$_2$CO$_3$ (resulting solution at pH 10) was added methoxycarbonyloxysuccinimide (187 mg, 1.1 mmol) dissolved in 5 mL. Afterwards, the reaction mixture was stirred at room temperature for 2 h. The alkaline solution was extracted once with ether (10 mL) and the aqueous phase was acidified with 1N HCl. This was extracted twice with 20 mL EtOAc, and the combined organic phases were washed with 50 mL 1N HCl. The organic phase was dried over Na$_2$SO$_4$, filtered and evaporated to an oil, which solidifies to yields 200 mg (73%) of the desired material. This intermediate (referred as the N-substituted amino acid) was used without further purification in the next step.

Step D. Preparation of (1S,5S)-(1-{5-[(4-amino-benzenesulfonyl)-isobutyl-amino]-6-phosphonooxy-hexylcarbamoyl}-2-naphthalen-2-yl-ethyl)-carbamic acid methyl ester (PL-507)

100 mg L-Moc-2-naphthylalanine (step C) was activated with 100 mg EDAC and 57 mg HOBt in 1.5 mL DMF for 30 minutes. Then, 100 mg of phosphoric acid 6-amino-2-[(4-amino-benzenesulfonyl)-isobutyl-amino]-hexyl ester diethyl ester (step B) was added and left to stir at room temperature for 1 h. 40 mL of 1M K$_2$CO$_3$ was added to the DMF solution and left for 10 min. 50 mL of EtOAc was then added and the mixture was then agitated vigorously. Separation of the EtOAc phase was effected, followed by extraction with 5% citric acid (50 mL) once, then water (50 mL) 3 times and finally brine. The organic phase was separated and evaporated. The residue was taken up in 50 mL DCM and re-evaporated. The residue was again taken up in 50 mL DCM and 0.5 mL of TMSBr was added. The solution was left overnight (16 h). The DCM was evacuated and a solution of ice cold MeOH:Water 1:1 was added, stirred briefly and evacuated. The residue was triturated with ether then dissolved in 1N NaOH. The clear solution was extracted with ether and the aqueous phase acidified with 6N HCl. The white precipitated was then collected by filtration and dried in vacuo overnight. Yields 88 mg of the title compound.

LC-MS: 679.8 (M+H)$^+$, 95% pure.

$^1$H NMR (CD$_3$OD): δ 0.89-0.98 (m, 8H), 1.15 (m, 2H), 1.35 (m, 1H), 1.45 (m, 1H), 1.88 (m, 1H), 2.84 (m, 2H), 2.98 (m, 1H), 3.01 (m, 2H), 3.24 (m, 1H), 3.56 (s, 3H), 3.60 (m, 1H), 3.81 (m, 1H), 3.99 (m, 1H), 4.39 (t, J=6.8, 1H), 6.91 (d, J=8.0, 2H), 7.34 (d, J=8.0, 1H), 7.45 (m, 2H), 7.58 (d, J=8.0, 2H), 7.66 (s, 1H), 7.70-7.82 (m, 3H). $^{31}$P NMR (CD$_3$OD): δ 2.56

Example 4

Preparation of (2S,2S) phosphoric acid mono-(2-[(4-amino-benzenesulfonyl)-isobutyl-amino]-6-{2-[(morpholine-4-carbonyl)-amino]-3-naphthalen-1-yl-propionylamino}-hexyl) ester (PL-498)

Step A. Preparation of (2S)-2-[(morpholine-4-carbonyl)-amino]-3-naphthalen-1-yl-propionic acid To a solution of L-1-naphthylalanine (215 mg, 1 mmol) (Peptech Corp.) in 5 mL 1N NaOH and 0.5 mL saturated Na$_2$CO$_3$ (resulting solution at pH 10) was added morpholine-4-carbonyl chloride (150 mg, 1.0 mmol) dissolved in 5 mL. Afterwards, the reaction mixture was stirred at room temperature for 2 h. The alkaline solution was extracted once with ether (10 mL) and the aqueous phase was acidified with 1N HCl. This was extracted twice with 20 mL EtOAc, and the combined organic phases were washed with 50 mL 1N HCl. The organic phase was dried over Na$_2$SO$_4$, filtered and evaporated to an oil, which solidifies to yields 125 mg (38%) of the desired material. This compound was used as such in the next step.

Step B. Preparation of (2S,2S) Phosphoric acid mono-(2-[(4-amino-benzenesulfonyl)-isobutyl-amino]-6-{2-[(morpholine-4-carbonyl)-amino]-3-naphthalen-1-yl-propionylamino}-hexyl) ester (PL-498)

This compound was made as for the preparation of the product of example 3 (step D) with 100 mg of (2S)-2-[(morpholine-4-carbonyl)-amino]-3-naphthalen-1-yl-propionic acid (step A of this example). The resulting precipitated residue was further purified by reverse phase preparative HPLC. Yields 41 mg of the final compound.

LC-MS: 734.8 (M+H)$^+$, 95% pure.

$^1$H NMR (CD$_3$OD): δ 0.83-0.98 (m, 8H), 1.00-1.25 (m, 4H), 1.45-1.52 (m, 1H), 1.52-1.66 (m, 1H), 1.88-1.99 (m, 1H), 2.77-2.92 (m, 2H), 2.98-3.16 (m, 3H), 3.40-3.49 (m, 1H), 3.50-3.56 (m, 6H), 3.67-3.69 (m, 1H), 3.81-3.89 (m, 1H), 3.99-4.05 (m, 1H), 4.59 (t, J=6.0, 1H), 6.75 (d, J=8.0, 2H), 7.30-7.60 (m, 7H), 7.75 (d, J=8.0, 1H), 7.90 (d, J=7.8, 1H), 8.23 (d, J=7.8 2H).

$^{31}$P NMR (CD$_3$OD): δ 2.71

Example 5

Preparation of (2S,2S)-phosphoric acid mono-{6-(2-acetylamino-3,3-diphenyl-propionylamino)-2-[(4-amino-benzenesulfonyl)-isobutyl-amino]-hexyl}ester (PL-504)

Step A. Preparation (2S)-2-acetylamino-3,3-diphenyl-propionic acid

To a solution of L-diphenylalanine (100 mg, 0.4 mmol) (Peptech Corp.) in 5 mL 1N NaOH and 0.5 mL saturated $Na_2CO_3$ (resulting solution at pH 10) was added acetyl chloride (0.5 mmol) dissolved in 5 mL. Afterwards, the reaction mixture was stirred at room temperature for 2 h. The alkaline solution was extracted once with ether (10 mL) and the aqueous phase was acidified with 1N HCl. This was extracted twice with 20 mL EtOAc, and the combined organic phases were washed with 50 mL 1N HCl. The organic phase was dried over $Na_2SO_4$, filtered and evaporated to an oil, which solidifies to yields 70 mg (60%) of the desired material. This crude intermediate was used as such in the next step.

Step B. Preparation of (2S,2S)-phosphoric acid mono-{6-(2-acetylamino-3,3-diphenyl-propionylamino)-2-[(4-amino-benzenesulfonyl)-isobutyl-amino]-hexyl}ester (PL-504)

This compound was made as for the preparation of the product of example 3 (step D) with 100 mg of (2S)-2-acetylamino-3,3-diphenyl-propionic acid (this example step A). The final product was obtained in 30% yield (30 mg).

LC-MS: 689.3 (M+H)$^+$, 95% pure.

$^1$H NMR (CD$_3$OD): δ 0.77-1.04 (m, 9H), 1.10-1.17 (m, 1H), 1.23-1.49 (m, 1H), 1.46-1.57 (m, 1H), 1.78 (s, 3H), 1.88-1.99 (m, 1H), 2.80-2.92 (m, 2H), 2.92-3.08 (m, 2H), 3.63-3.75 (m, 1H), 3.79-3.95 (m, 1H), 4.00 (m, 1H), 4.34 (d, J=11.3, 1H), 5.19-5.28 (m, 1H), 6.77-6.85 (m, 2H), 7.10-7.20 (m, 2H), 7.27-7.33 (m, 6H), 7.32-7.41 (m, 2H), 7.49-7.62 (m, 2H). $^{31}$P NMR (CD$_3$OD): δ 2.70

Example 6

Preparation of (1S,5S)-(1-{5-[(4-amino-3-fluoro-benzenesulfonyl)-isobutyl-amino]-6-phosphonooxy-hexylcarbamoyl}-2,2-diphenyl-ethyl)-carbamic acid methyl ester (PL-515)

First methodology: The preparation of the title compound is based on scheme 3 of this invention.

Step A. Preparation of (1-{5-[(4-amino-3-fluoro-benzenesulfonyl)-isobutyl-amino]-6-hydroxy-hexylcarbamoyl}-2,2-diphenyl-ethyl)-carbamic acid methyl ester (X) (PL-337)

The product of example 1, step F (0.624 g, 1 mmol) is dissolved in 5 mL MeCN at 24° C. SelectFluor 0.35 g (1 mmol) is added in one portion and stirred for 1 h. 1 mL of water is added and the solution was injected directly into a preparative reverse-phase HPLC. The product was collected and lyophilized to give 250 mg (38%) yield of a white solid.

LC-MS: 643.3 (M+H)$^+$, 99% pure.

$^1$H NMR (MeOD): δ 0.71-0.85 (m 2H), 0.88 (d, J=6.3, 6H), 0.91-0.96 (m, 2H), 1.21-1.29 (m, 1H), 1.41-1.52 (m, 1H) 1.82-1.92 (m, 1H), 2.61-2.68 (m, 2H), 2.81-2.85 (m, 2H), 2.94-3.05 (m, 2H), 3.38-3.40 (t, J=5, 1H), 3.49-3.52 (m, 5H), 4.28 (d, J=10, 1H), 4.87 (d, J=10, 1H) 6.90 (t, J=8.3, 1H), 7.20 (m, 2H), 7.28 (m, 3H), 7.33 (m, 3H), 7.39 (m, 4H).

Step B. Preparation of (1S,5S)-{1-[5-[(4-amino-3-fluoro-benzenesulfonyl)-isobutyl-amino]-6-(diethoxy-phosphoryloxy)-hexylcarbamoyl]-2,2-diphenyl-ethyl}-carbamic acid methyl ester The product of step A was phosphorylated with chlorodiethylphosphate following the procedure described in example 1, step G. Yields 157 mg, 68%.

LC-MS: 779.3 (M+H)$^+$, 95% pure.

$^1$H NMR (CD$_3$OD): δ 0.82 (m, 1H), 0.92 (d, J=6.2, 8H), 0.96 (m, 3H), 1.36 (d, J=3.7, 6H), 1.90 (m, 1H), 2.69 (m, 1H), 2.89 (m, 1H), 2.98 (m, 2H), 3.56 (s, 3H), 3.74 (m, 1H), 3.93 (m, 1H), 4.03 (m, 1H), 4.12 (q, J=7.5 and 14.8, 4H), 4.32 (d, J=11.4, 1H), 4.92 (d, J=11.4, 1H), 6.90 (t, J=8.3, 1H), 7.20 (m, 2H), 7.28 (m, 3H), 7.33 (m, 3H), 7.39 (m, 4H).

$^{31}$P NMR (CD$_3$OD): δ 1.65

Step C. Preparation of (1S,5S)-(1-{5-[(4-amino-3-fluoro-benzenesulfonyl)-isobutyl-amino]-6-phosphonooxy-hexylcarbamoyl}-2,2-diphenyl-ethyl)-carbamic acid methyl ester (XI) (PL-515)

Deprotection was effected using the procedure described in example 1, step G. Yields 101 mg.

LC-MS: 723.2 (M+H)$^+$, 95% pure.

$^1$H NMR (CD$_3$OD): δ 0.65-0.77 (m, 1H), 0.77-0.85 (m, 1H), 0.85-1.05 (m, 9H), 1.25-1.39 (m, 1H), 1.40-1.52 (m, 1H), 1.82-1.98 (m, 1H), 2.58-2.72 (m, 1H), 2.82-2.92 (m, 1H), 2.92-3.05 (m, 2H), 3.54 (s, 3H), 3.64-3.75 (m, 1H), 3.80-3.92 (m, 1H), 3.91-4.04 (m, 1H), 4.29 (d, J=11.4, 1H), 7.19 (t, J=6.6, 1H), 7.13-7.21 (m, 2H), 7.22-7.33 (m, 6H), 7.34-7.38 (m, 2H), 7.39-7.48 (m, 2H).

$^{31}$P NMR (CD$_3$OD): δ 2.74

Second methodology: The preparation of the title compound is based on scheme 4 of this invention.

Step A. Preparation (1S,5S)-(1-{5-[(4-amino-benzenesulfonyl)-isobutyl-amino]-6-phosphonooxy-hexylcarbamoyl}-2,2-diphenyl-ethyl)-carbamic acid methyl ester (PL-461)

(2S)-2-methoxycarbonylamino-3,3-diphenyl-propionic acid ((example 1, step E) 0.9 g, 3 mmol) was activated in DMF (5 mL) with EDAC (1.7 g, 9 mmol) and HOBt (1.2 g, 9 mmol). To the solution was added 1.17 g of (2S)-phosphoric acid 6-amino-2-[(4-amino-benzenesulfonyl)-isobutyl-amino]-hexyl ester diethyl ester (IX) (example 3, step B) and the mixture stirred for 3 h. 20 g of Amberlite XAD-2 resin was then added and the beads were left to soak for 10 min. The resin was transferred into a glass filter and washed thoroughly with distilled water (400 mL) and 200 mL of 1M NaHCO$_3$. The beads were then washed with 4×50 ml portions of MeOH then EtOAc 200 mL. The organic phase was evaporated. The residue was adsorbed onto silica gel and passed through a short silica gel column (EtOAc) to yield 2.4 g (83%) of white solid after evaporation.

NMR identical as in example 1, step H.

Step B. Preparation (1S,5S)-{1-[5-[(4-amino-3-fluoro-benzenesulfonyl)-isobutyl-amino]-6-(diethoxy-phosphoryloxy)-hexylcarbamoyl]-2,2-diphenyl-ethyl}-carbamic acid methyl ester (XII)

The product of step A above, (1S,5S)-(1-{5-[(4-amino-benzenesulfonyl)-isobutyl-amino]-6-phosphonooxy hexyl-carbamoyl}-2,2-diphenyl-ethyl)-carbamic acid methyl ester (0.555 g, 0.73 mmol) was dissolved in 5 mL MeCN. Selectfluor (0.26 g, 0.7 mmol) was added and the mixture stirred for 30 min. The mixture was purified by reverse phase preparative HPLC and lyophilized to yield 278 mg (48% yield) white solid.

$^1$H NMR identical as previous entry, see first methodology above.

Step C. Preparation (1S,5S)-(1-{5-[(4-amino-3-fluoro-benzenesulfonyl)-isobutyl-amino]-6-phosphonooxy-hexylcarbamoyl}-2,2-diphenyl-ethyl)-carbamic acid methyl ester (XIII, in this Specific Case is Compound XI) (PL-515)

The procedure make this derivative was as described in the deprotection step for the methodology above. Yields 139 mg 70% after reverse phase HPLC.

$^1$H NMR identical as previous entry, see first methodology above.

Example 7

Preparation of (2S,2S)-acetic acid 2-[(4-amino-benzenesulfonyl)-isobutyl-amino]-6-(2-methoxycarbonylamino-3,3-diphenyl-propionylamino)-hexyl ester (PL-521)

The preparation of the title derivative is based on scheme 5 of this invention.

Step A. Preparation of (2S)-acetic acid 6-tert-butoxycarbonylamino-2-[(4-tert-butoxycarbonylamino-benzenesulfonyl)-isobutyl-amino]-hexyl ester (XIV, $R_{1A}$=CH$_3$)

To a stirred solution of (1S)-{4-[(5-tert-butoxycarbonylamino-1-hydroxymethyl-pentyl)-isobutyl-sulfamoyl]-phenyl}-carbamic acid tert-butyl ester (intermediate product (VII) of example 1, step D, 97 mg, 0.18 mmol) in anhydrous CH$_2$Cl$_2$ (3 mL) was added N,N-dimethylaminopyridine (22 mg, 0.18 mmol) and acetic anhydride (0.014 mL, 0.18 mmol). The mixture was stirred at room temperature for 1 hour. The solvent was evaporated. Ethyl acetate (50 mL) was added and the organic layer was washed with water (30 mL), then dried with Na$_2$SO$_4$ and concentrated. The residue was purified by flash chromatography eluting with ethyl acetate. The yield obtained was quantitative (100 mg).

LC-MS: 586.2 (M+H)$^+$, 95% pure

Step B. Preparation of (2S)-acetic acid 6-amino-2-[(4-amino-benzenesulfonyl)-isobutyl-amino]-hexyl ester (XV, $R_{1A}$=CH$_3$)

This derivative was prepared from (2S)-acetic acid 6-tert-butoxycarbonylamino-2-[(4-tert-butoxycarbonylamino-benzenesulfonyl)-isobutyl-amino]-hexyl ester as described in example 15, step B. The yellow solid (66 mg) was used for the next reaction without purification.

LC-MS: 386.2 (M+H)$^+$, 95% pure

Step C. Preparation of (2S,2S)-acetic acid 2-[(4-amino-benzenesulfonyl-)isobutyl-amino]-6-(2-methoxycarbonylamino-3,3-diphenyl-propionylamino)-hexyl ester (XVI, $R_{1A}$=CH$_3$) (PL-521)

This derivative was prepared from (2S)-acetic acid 6-amino-2-[(4-amino-benzenesulfonyl)-isobutyl-amino]-hexyl ester (product of step B) as described in example 15, step B. The final product was purified by flash chromatography with a mixture of eluents hexane/ethyl acetate (2/8). A yellow solid was obtained in 70% yield (70 mg).

LC-MS: 667.3 (M+H)$^+$, 95% pure $^1$H NMR (acetone-d$_6$): δ 0.85-0.97 (m, 12H), 1.21-1.41 (m, 2H), 1.88-2.00 (s, 3H), 2.59-2.69 (m, 1H), 2.83-2.90 (m, 1H), 2.90-3.01 (m, 1H), 3.01-3.10 (br s, 1H), 3.45-3.60 (s, 3H), 3.70-3.80 (m, 1H), 3.93-4.00 (m, 1H), 4.00-4.11 (m, 1H), 4.38-4.45 (d, J=11.0, 1H), 4.89-4.98 (t, J=10.0, 1H), 5.43-5.58 (br s, 1H), 6.28-6.48 (d, J=8.9, 1H), 6.72-6.83 (d, J=8.0, 2H), 6.85-6.93 (br s, 1H), 7.12-7.22 (t, J=7.4, 1H), 7.21-7.31 (d, J=7.0, 4H), 7.31-7.45 (m, 5H), 7.48-7.57 (d, J=8.0, 2H).

Example 8

Preparation of (2S,2S)-nicotinic acid 2-[(4-amino-benzenesulfonyl)-isobutyl-amino]-6-(2-methoxycarbonylamino-3,3-diphenyl-propionylamino)-hexyl ester (PL-520)

Step A. Preparation of (2S)-nicotinic acid 6-tert-butoxycarbonylamino-2-[(4-tert-butoxycarbonylamino-benzenesulfonyl)-isobutyl-amino]-hexyl ester (XIV, $R_{1A}$=3-pyridyl)

(1S)-{4-[(5-tert-butoxycarbonylamino-1-hydroxymethyl-pentyl)-isobutyl-sulfamoyl]-phenyl}-carbamic acid tert-butyl ester (intermediate product (yl) of example 1, step D, 130 mg, 0.24 mmol) was dissolved in anhydrous DMF (1 mL) and treated with 0.066 mL (0.48 mmol) of triethylamine followed by EDC (120 mg, 0.65 mmol), HOBt (88 mg, 0.65 mmol) and nicotinic acid (27 mg, 0.22 mmol). The mixture was stirred overnight at room temperature. The product was extracted with ethyl acetate (40 mL) and water (40 mL). The organic phase was separated and dried with Na$_2$SO$_4$, then evaporated to give 200 mg of crude product. This compound was purified by flash chromatography with ethyl acetate as the eluent. A clear oil was obtained in 100% yield (150 mg).

LC-MS: 649.3 (M+H)$^+$, 95% pure $^1$H NMR (acetone-d$_6$): δ 0.90-1.14 (d, J=5.9, 6H), 1.31-1.42 (m, 2H), 1.48 (s, 9H), 1.51-1.55 (m, 2H), 1.59 (s, 9H), 1.62-1.69 (m, 1H), 1.72-1.83 (m, 1H), 3.00-3.11 (m, 2H), 3.11-3.17 (m, 1H), 3.19-3.27 (m, 1H), 4.15-4.24 (m, 1H), 4.35-4.44 (t, J=9.1, 1H), 4.50-4.58 (dd, J=4.4 and 11.5, 1H), 5.89-5.99 (br s, 1H), 7.53-7.60 (m, 1H), 7.70-7.77 (d, J=8.2, 2H), 7.80-7.87 (d, J=8.2, 2H), 8.24-8.31 (d, J=7.3, 1H), 8.75-8.82 (m, 1H), 8.82-8.88 (m, 1H), 9.12-9.18 (br s, 1H).

Step B. Preparation of (2S)-nicotinic acid 6-amino-2-[(4-amino-benzenesulfonyl)-isobutyl-amino]-hexyl ester (XV, $R_{1A}$=3-pyridyl)

The product of step A, (2S)-nicotinic acid 6-tert-butoxycarbonylamino-2-[(4-tert-butoxycarbonylamino-benzenesulfonyl)-isobutyl-amino]-hexyl ester (150 mg, 0.23 mmol), was dissolved in CH$_2$Cl$_2$ (5 mL) and trifluoroacetic acid (1 mL) was added. The mixture was stirred during 2 hours at room temperature. The solvent was evaporated and the residue was extracted with ethyl acetate (40 mL) and NaOH 1M (40 mL) (pH=10). The organic portion was separated, dried with Na$_2$SO$_4$ and evaporated. The residue (100 mg) was used for the next reaction without further purification. The yield was quantitative.

LC-MS: 449.2 (M+H)$^+$, 95% pure

Step C. Preparation of (2S,2S)-nicotinic acid 2-[(4-amino-benzenesulfonyl)-isobutyl-amino]-6-(2-methoxycarbonylamino-3,3-diphenyl-propionylamino)-hexyl ester (PL-520)

The product of step B, (2S)-nicotinic acid 6-amino-2-[(4-amino-benzenesulfonyl)-isobutyl-amino]-hexyl ester (100 mg, 0.22 mmol) was dissolved in anhydrous. DMF (2 mL) and treated with 0.062 mL (0.45 mmol) of triethylamine followed by EDC (100 mg, 0.56 mmol), HOBt (75 mg, 0.56 mmol) and (2S)-2-methoxycarbonylamino-3,3-diphenyl-propionic acid (56 mg, 0.19 mmol). The mixture was stirred overnight at room temperature. The product was extracted with ethyl acetate (40 mL) and water (40 mL). The organic layer was separated and dried with $Na_2SO_4$, then evaporated to give 160 mg of crude oil. The residue was purified by flash chromatography with a mixture of eluents hexane/ethyl acetate (2/8). The title compound was obtained as a clear oil in 20% yield (25 mg).

LC-MS: 730.2 $(M+H)^+$, 95% pure $^1$H NMR (acetone-$d_6$): δ 0.80-0.97 (m, 9H), 0.97-1.13 (m, 2H), 1.26-1.40 (m, 1H), 1.40-1.57 (m, 1H), 2.61-2.73 (m, 1H), 2.86-2.98 (m, 2H), 3.00-3.17 (m, 2H), 3.45-3.59 (s, 3H), 3.91-4.00 (m, 1H), 4.24-4.34 (m, 1H), 4.34-4.47 (m, 2H), 4.90-4.99 (t, J=9.7, 1H), 6.35-6.44 (m, 1H), 6.68-6.79 (d, J=7.9, 1H), 6.91-7.00 (br s, 1H), 7.13-7.22 (m, 2H), 7.22-7.31 (m, 3H), 7.35-7.48 (m, 4H), 7.49-7.64 (m, 2H), 7.75-7.84 (m, 1H), 8.25-8.36 (m, 1H), 8.76-8.88 (br s, 1H), 9.12-9.26 (br s, 1H).

Example 9

Preparation of (2S,2S)-dimethylamino-acetic acid 2-[(4-amino-benzenesulfonyl)-isobutyl-amino]-6-(2-methoxycarbonylamino-3,3-diphenyl-propionylamino)-hexyl ester (PL-534)

Step A. Preparation of (2S)-dimethylamino-acetic acid 6-tert-butoxycarbonylamino-2-[(4-tert-butoxycarbonylamino-benzenesulfonyl)-isobutyl-amino]-hexyl ester (XIV, $R_{1A}$=$(CH_3)_2NCH_2$—)

This title compound was obtained from (1S)-{4-[(5-tert-butoxycarbonylamino-1-hydroxymethyl-pentyl)-isobutyl-sulfamoyl]-phenyl}-carbamic acid tert-butyl ester (intermediate product (VII) of example 1, step D) as described example 15, step A using N,N-dimethylglycine. The clear oil was obtained in 100% yield (150 mg).

LC-MS: 629.3 $(M+H)^+$, 95% pure $^1$H NMR (acetone-$d_6$): δ 0.81-0.95 (d, J=6.1, 6H), 1.18-1.30 (m, 2H), 1.32-1.43 (s, 9H), 1.43-1.52 (s, 8H), 1.52-1.62 (m, 1H), 1.93-2.00 (m, 1H), 2.19-2.29 (s, 4H), 2.69-2.80 (m, 4H), 2.90-3.05 (m, 6H), 3.60-3.65 (m, 1H), 3.85-3.97 (m, 1H), 3.98-4.08 (m, 1H), 4.08-4.14 (m, 1H), 5.78-5.88 (m, 1H), 7.68-7.80 (m, 3H), 8.80-8.88 (br s, 1H).

Step B. Preparation of (2S)-dimethylamino-acetic acid 6-amino-2-[(4-amino-benzenesulfonyl)-isobutyl-amino]-hexyl ester (XV, $R_{1A}$=$(CH_3)_2NCH_2$—)

The title derivative was prepared from (2S)-dimethylamino-acetic acid 6-tert-butoxycarbonylamino-2-[(4-tert-butoxycarbonylamino-benzenesulfonyl)-isobutyl-amino]-hexyl ester as described in example 15, step B. The final product (100 mg) was used as such in the next step.

LC-MS: 429.3 $(M+H)^+$, 90% pure

Step C. Preparation of (2S,2S)-dimethylamino-acetic acid 2-[(4-amino-benzenesulfonyl)-isobutyl-amino]-6-(2-methoxycarbonylamino-3,3-diphenyl-propionylamino)-hexyl ester (PL-534)

This title compound was prepared from (2S)-dimethylamino-acetic acid 6-amino-2-[(4-amino-benzenesulfonyl)-isobutyl-amino]-hexyl ester as described in example 15, step C. The crude product was purified by LC-preparative. The final compound was obtained in 10% yield (10 mg).

LC-MS: 710.3 $(M+H)^+$, 92% pure $^1$H NMR (acetone-$d_6$): δ 0.81-0.98 (m, 12H), 1.14-1.30 (m, 2H), 1.31-1.45 (m, 1H), 2.58-2.77 (m, 2H), 2.79-2.90 (m, 2H), 3.42-3.56 (s, 3H), 3.75-3.85 (m, 1H), 3.99-4.17 (m, 3H), 4.23-4.35 (m, 1H), 4.36-4.45 (m, 1H), 4.86-4.96 (m, 1H), 6.33-6.42 (m, 1H), 6.74-6.83 (m, 1H), 6.85-6.90 (m, 1H), 7.12-7.22 (m, 3H), 7.23-7.31 (m, 4H), 7.31-7.44 (m, 5H), 7.47-7.55 (m, 1H), 7.73-7.80 (m, 1H).

Example 10

Preparation of (2S,2S)-2-amino-3-methyl-butyric acid 2-[(4-amino-benzenesulfonyl)-isobutyl-amino]-6-(2-methoxycarbonylamino-3,3-diphenyl-propionylamino)-hexyl ester (PL-530)

Step A. Preparation of (2S)-2-benzyloxycarbonylamino-3-methyl-butyric acid 6-tert-butoxycarbonylamino-2-[(4-tert-butoxycarbonylamino-benzenesulfonyl)-isobutyl-amino]-hexyl ester (XIV, $R_{1A}$=$(CH_3)_2CHCH(NH_2)$—)

This title compound was obtained from (1S)-{4-[(5-tert-butoxycarbonylamino-1-hydroxymethyl-pentyl)-isobutyl-sulfamoyl]-phenyl}-carbamic acid tert-butyl ester (intermediate product (VII) of example 1, step D) as described in example 15, step A using (2S)-2-benzyloxycarbonylamino-3-methyl-butyric acid. The crude product was purified by flash chromatography eluting with a mixture of hexane/ethyl acetate (1/1). The yield obtained was 100% (150 mg).

LC-MS: 777.3 $(M+H)^+$, 95% pure $^1$H NMR (acetone-$d_6$): δ 0.80-1.00 (m, 14), 1.13-1.28 (s, 2H), 1.30-1.44 (s, 11H), 1.45-1.56 (s, 10), 1.58-1.67 (m, 1H), 2.87-3.04 (m, 4H), 3.84-3.97 (m, 1H), 3.97-4.12 (m, 2H), 4.12-4.21 (m, 1H), 4.99-5.14 (m, 2H), 5.78-5.89 (m, 1H), 6.38-6.52 (m, 1H), 7.24-7.34 (m, 1H), 7.34-7.41 (m, 2H), 7.65-7.83 (m, 4H), 8.77-8.86 (m, 1H).

Step B. Preparation of (2S)-benzyloxycarbonylamino-3-methyl-butyric acid 6-amino-2-[(4-amino-benzenesulfonyl)-isobutyl-amino]-hexyl ester (XV, $R_{1A}$=$(CH_3)_2CHCH(NH_2)$—)

This derivative was prepared from (2S)-2-benzyloxycarbonylamino-3-methyl-butyric acid 6-tert-butoxycarbonylamino-2-[(4-tert-butoxycarbonylamino-benzenesulfonyl)-isobutyl-amino]-hexyl ester (product of step A) as described in example 15, step B. The final compound was obtained in quantitative yield (110 mg) and used for the next step without purification.

LC-MS: 577.3 $(M+H)^+$, 90% pure

Step C. Preparation of (2S,2S)-2-benzyloxycarbonylamino-3-methyl-butyric acid 2-[(4-amino-benzenesulfonyl)-isobutyl-amino]-6-(2-methoxycarbonylamino-3,3-diphenyl-propionylamino)-hexyl ester The title compound was obtained from (2S)-benzyloxycarbonylamino-3-methyl-butyric acid 6-amino-2-[(4-amino-benzenesulfonyl)-isobutyl-amino]-hexyl ester (product of step B) as described in example 15, step C. The clear oil was obtained in 86% yield (120 mg).

LC-MS: 858.3 (M+H)$^+$, 95% pure

Step D. Preparation of (2S,2S)-2-amino-3-methyl-butyric acid 2-[(4-amino-benzenesulfonyl)-isobutyl-amino]-6-(2-methoxycarbonylamino-3,3-diphenyl-propionylamino)-hexyl ester (PL-530)

To a stirred solution of (2S,2S)-2-benzyloxycarbonylamino-3-methyl-butyric acid 2-[(4-amino-benzenesulfonyl)-isobutyl-amino]-6-(2-methoxycarbonylamino-3,3-diphenyl-propionylamino)-hexyl ester (step C, 120 mg, 0.14 mmol) in anhydrous THF (8 mL), under nitrogen atmosphere, was added palladium 10% wt. on activated carbon (160 mg). The mixture was reacted under hydrogen atmosphere overnight, at room temperature. The solution was filtered and the palladium on carbon was washed with THF (50 mL). The solvent was evaporated and the residue (110 mg) was purified by flash chromatography using ethyl acetate as the eluent. The clear oil was obtained in 47% yield (47 mg).

LC-MS: 796.4 (M+H)$^+$, 95% pure $^1$H NMR (acetone-d$_6$): δ 0.84-0.97 (m, 12H), 0.97-1.08 (m, 2H), 1.27-1.43 (m, 3H), 1.49-1.62 (m, 4H), 1.80-1.93 (m, 1H), 1.94-2.00 (m, 1H), 2.36-2.46 (m, 1H), 2.58-2.74 (m, 2H), 2.86-2.96 (m, 3H), 2.99-3.10 (m, 2H), 3.46-3.52 (s, 3H), 3.52-3.60 (m, 2H), 3.75-3.87 (m, 2H), 3.95-4.04 (m, 1H), 4.10-4.18 (m, 1H), 4.37-4.44 (m, 1H), 4.89-4.97 (m, 1H), 5.40-5.48 (m, 1H), 6.30-6.40 (m, 1H), 6.76-6.83 (d, J=8.2, 1H), 6.87-7.03 (m, 2H), 7.14-7.22 (m, 1H), 7.23-7.34 (m, 3H), 7.35-7.45 (m, 4H), 7.50-7.56 (m, 1H), 7.57-7.65 (m, 1H).

Bioavailability of the Compounds

To assess the extent of in vivo cleavage of the phosphate group from the putative compounds, PL-100, PL-462 (based on PL-100), PL-337 and PL-515 (based on PL-337) compounds were administered po (50 mg/kg) to male Sprague-Dawley rats and their plasma concentration measured at different time intervals post-administration.

PL100 is an active ingredient (protease inhibitor) of the following formula;

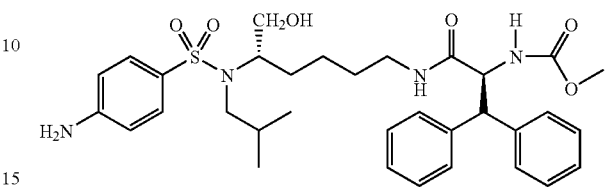

PL-337 is an active ingredient (protease inhibitor) of the following formula;

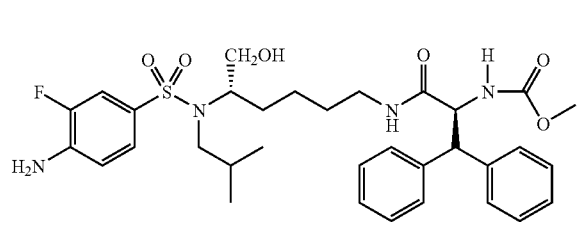

The active ingredient has been shown to be efficient against an HIV-1 aspartyl protease (U.S. Pat. No. 6,632,816). The active ingredients also present potent antiviral activity when tested on non-mutated HIV-1 viral strain (NL4.3 as the wild type virus) as well as several mutant strains.

All test articles (PL-100, PL-462, PL-337 and PL-515) were prepared in different vehicle at the final concentration of 25 mg/mL. The vehicle composition is as follows: (1) 20% ethanol; 50% propylene glycol; 0.05% w/v Tween 20 and water (Mix); (2) PBS buffer (PBS).

Test articles were administered to male Sprague-Dawley rats at a single oral dose of 50 mg/kg. Each article was tested in three rats. Blood samples (0.2-0.3 mL) were collected at the post-dose time of 10, 20, 40, 60, 120, 180 and 360 minutes. The harvested blood was centrifuged to isolate plasma. The resulting plasma was separated and stored at −70° C.

Plasma samples together with standards and quality control samples were treated to precipitate proteins, then analyzed by HPLC-MS, for the presence of PL-462, PL-100, PL-515 and PL-337.

TABLE 1

| Compound | PL-462 (Ex. No. 2) | PL-100 (Ex. No. 1-F) | PL-515 (Ex. No. 13) | PL-337 (Ex. No. 13-A) |
| --- | --- | --- | --- | --- |
| Vehicle | PBS | Mix | PBS | Mix |
| Number of rats | 3 | 3 | 3 | 3 |
| Dose (mg/Kg) | 50 po | 50 po | 50 po | 50 po |
| AUC (µg/hr*ml) | 0.816 ± 0.295 (PL-100, detected) | 0.675 ± 0.171 | 1.075 ± 0.625 (PL-337, detected) | 1.180 ± 0.196 |
| Cmax (nM) | 330 ± 109 | 498 ± 203 | 545 ± 215 | 681 ± 131 |
| Tmax (min) | 93 ± 60 | 40 ± 16 | 87 ± 60 | 60 ± 15 |

50 mg/Kg PL-462 = 43 mg/Kg PL-100

50 mg/Kg PL-515 = 43 mg/Kg PL-337

The results demonstrate that PL-462 and PL-515 compounds may be delivered orally in aqueous solutions. None of the PL-462 and PL-515 compounds, delivered as aqueous solutions, are detected in the blood samples, which suggests rapid metabolism to PL-100 and PL-337 the parent drugs.

Aqueous dosing of PL-462 and PL-515 solutions showed equivalent to slightly superior delivery of PL-100 and PL-337 compared to non-aqueous formulations of PL-100 and PL-337.

Based on these results, all the phosphorylated compounds described in the present invention will demonstrate similar pharmacokinetic properties.

Partition coefficient (LogP) of selected compounds and the corresponding HIV protease inhibitors (drug) are as follow:

TABLE

| Compounds | LogP | Corresponding drugs | LogP |
|---|---|---|---|
| PL-461 (or PL-462) | −1.2 | PL-100 | 3.6 |
| PL-515 | −0.75 | PL-337 | 3.8 |

The LogP were measured in a standard fashion by dissolving 1 mg of compound in 0.8 mL of each octanol and phosphate buffer pH 7.4 (0.04 M $KHPO_4$). The concentration of the compounds in the phases was detected by LC-MS. This test demonstrates the solubility of the compounds at physiological pH. The LogP obtained show that the compounds are highly soluble as compare to the corresponding drugs.

The compounds listed in Table 3 were prepared by following scheme 1, 1A, 2, 3, 4 or 5; and more particularly as described in each example listed above. The numbers of the compounds listed in Table 3 (Ex. No.) corresponds to the example numbers presented above.

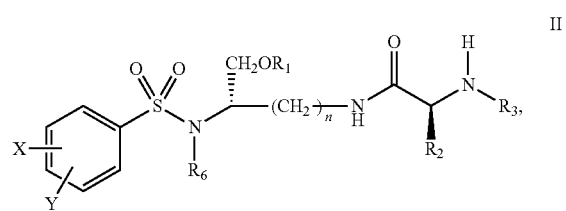

or a pharmaceutically acceptable salt thereof,
wherein n is 3 or 4,
wherein X and Y, the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_4R_5$, —NH-$COR_4$, —$OR_4$, —$SR_4$, —$COOR_4$, —$COR_4$, and —$CH_2OH$ or X and Y together define an alkylenedioxy group selected from the group consisting of a methylenedioxy group of formula —$OCH_2O$— and an ethylenedioxy group of formula —$OCH_2CH_2O$—,
wherein $R_6$ is selected from the group consisting of a straight alkyl group of 1 to 6 carbon atoms, a branched alkyl group of 3 to 6 carbon atoms and a cycloalkylalkyl group having 3 to 6 carbon atoms in the cycloalkyl part thereof and 1 to 3 carbon atoms in the alkyl part thereof,
wherein $R_3$ is selected from the group consisting of H, a straight alkyl group of 1 to 6 carbon atoms, a branched alkyl group of 3 to 6 carbon atoms, a cycloalkyl group of 3 to 6 carbon atoms, and a group of formula $R_{3A}$—CO—, $R_{3A}$ being selected from the group consisting of a straight or branched alkyl group of 1 to 6 carbon atoms, a cycloalkyl group having 3 to 6 carbon atoms, a

TABLE 3

Structures of lysine based compounds in accordance with the present invention

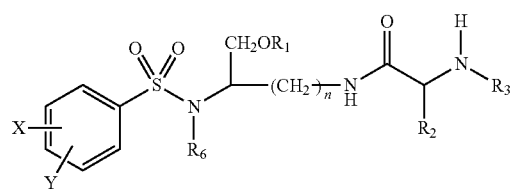

I

| Ex. No | (PL-#) | X | Y | n | $R_1$ | $R_2$ | $R_3$ | $R_6$ | X'/Y' | D, L, DL R, S, RS |
|---|---|---|---|---|---|---|---|---|---|---|
| 1 | (PL-461) | 4-$NH_2$ | H | 4 | $(HO)_2P(O)$ | $(C_6H_5)_2CH$ | $CH_3O$—CO | iso-butyl | H/H | S,S |
| 2 | (PL-462) | 4-$NH_2$ | H | 4 | $(NaO)_2P(O)$ | $(C_6H_5)_2CH$ | $CH_3O$—CO | iso-butyl | H/H | S,S |
| 3 | (PL-507) | 4-$NH_2$ | H | 4 | $(HO)_2P(O)$ | Naphthyl-2-$CH_2$ | $CH_3O$—CO | iso-butyl | H/H | S,S |
| 4 | (PL-498) | 4-$NH_2$ | H | 4 | $(HO)_2P(O)$ | Naphthyl-1-$CH_2$ | 4-morpholine-CO | iso-butyl | H/H | S,S |
| 5 | (PL-504) | 4-$NH_2$ | H | 4 | $(HO)_2P(O)$ | $(C_6H_5)_2CH$ | $CH_3CO$ | iso-butyl | H/H | S,S |
| 6 | (PL-515) | 4-$NH_2$ | 3-F | 4 | $(HO)_2P(O)$ | $(C_6H_5)_2CH$ | $CH_3O$—CO | iso-butyl | H/H | S,S |
| 7 | (PL-521) | 4-$NH_2$ | H | 4 | $CH_3CO$ | $(C_6H_5)_2CH$ | $CH_3O$—CO | iso-butyl | H/H | S,S |
| 8 | (PL-520) | 4-$NH_2$ | H | 4 | 3-Pyridyl-CO | $(C_6H_5)_2CH$ | $CH_3O$—CO | iso-butyl | H/H | S,S |
| 9 | (PL-534) | 4-$NH_2$ | H | 4 | $(CH_3)_2NCH_2CO$ | $(C_6H_5)_2CH$ | $CH_3O$—CO | iso-butyl | H/H | S,S |
| 10 | (PL-530) | 4-$NH_2$ | H | 4 | $(CH_3)_2CHCH(NH_2)CO$ | $(C_6H_5)_2CH$ | $CH_3O$—CO | iso-butyl | H/H | S,S |

We claim:

1. A method for treating or preventing an HIV infection or for delaying the appearance of AIDS, which comprises administering a compound of Formula II, cycloalkylalkyl group having 3 to 6 carbon atoms in the cycloalkyl part thereof and 1 to 3 carbon atoms in the alkyl part thereof, an alkyloxy group of 1 to 6 carbon atoms, tetrahydro-3-furanyloxy, —$CH_2OH$, —$CF_3$, —CH$_2$CF$_3$, —CH$_2$CH$_2$CF$_3$, pyrrolidinyl, piperidinyl, 4-morpholinyl, CH$_3$O$_2$C—, CH$_3$O$_2$CCH$_2$—, Acetyl-OCH$_2$CH$_2$—, HO$_2$CCH$_2$—, 3-hydroxyphenyl, 4-hydroxyphenyl, 4-CH$_3$OC$_6$H$_4$CH$_2$—, CH$_3$NH—, (CH$_3$)$_2$N—, (CH$_3$CH$_2$)$_2$N—, (CH$_3$CH$_2$CH$_2$)$_2$N—, HOCH$_2$CH$_2$NH—, CH$_3$OCH$_2$O—CH$_3$OCH$_2$CH$_2$O—, C$_6$H$_5$CH$_2$O—, 2-pyrrolyl, 2-pyridyl, 3-pyridyl, 4-pyridyl-, 2-pyrazinyl, 2-quinolyl, 3-quinolyl, 4-quinolyl, 1-isoquinolyl, 3-isoquinolyl, 2-quinoxalinyl, a phenyl group of formula

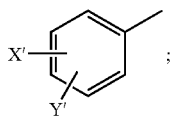

a picolyl group selected from the group consisting of

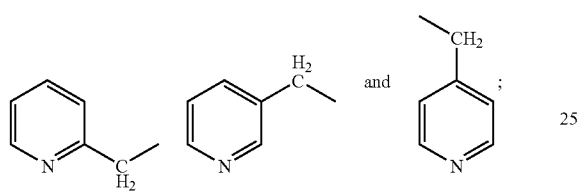

a picolyloxy group selected from the group consisting of

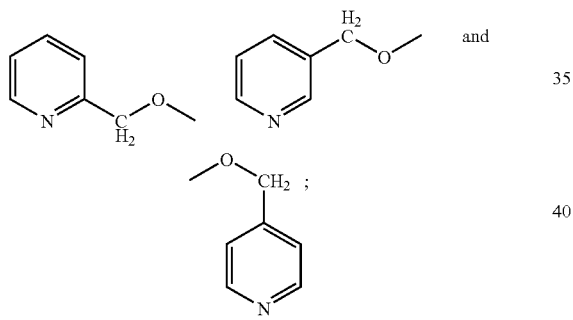

a substituted pyridyl group selected from the group consisting of

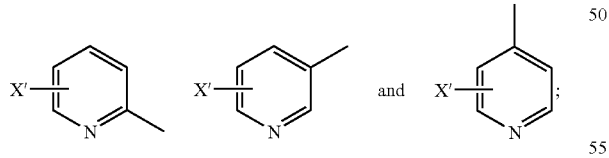

and a group of formula

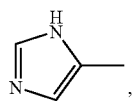

wherein X' and Y', the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —CF$_3$, —NO$_2$, —NR$_4$R$_5$, —NHCOR$_4$, —OR$_4$, —SR$_4$, —COOR$_4$, —COR$_4$ and —CH$_2$OH, wherein R$_4$ and R$_5$, the same or different, are selected from the group consisting of H, a straight alkyl group of 1 to 6 carbon atoms, a branched alkyl group of 3 to 6 carbon atoms, and a cycloalkyl group of 3 to 6 carbon atoms, wherein R$_2$ is selected from the group consisting of a diphenylmethyl group of formula IV,

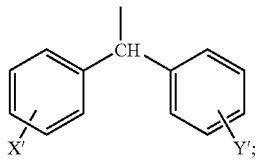

a naphthyl-1-CH$_2$— group of formula V,

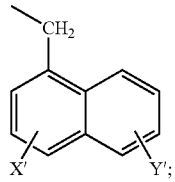

a naphthyl-2-CH$_2$— group of formula VI,

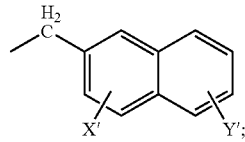

a biphenylmethyl group of formula VII,

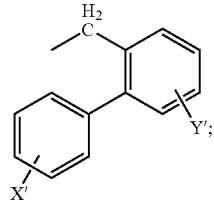

and an anthryl-9-CH$_2$— group of formula VIII,

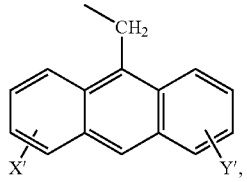

and wherein $R_1$ is selected from the group consisting of $(HO)_2P(O)$, $(MO)_2P(O)$ and a group of formula $R_{1A}$—CO—, wherein M is an alkali metal or alkaline earth metal, wherein $R_{1A}$ is selected from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part thereof and 1 to 3 carbon atoms in the alkyl part thereof, an alkyloxy group of 1 to 6 carbon atoms, —$CH_2OH$, $CH_3O_2C$—, $CH_3O_2CCH_2$—, Acetyl-$OCH_2CH_2$—, $HO_2CCH_2$—, 2-hydroxyphenyl, 3-hydroxyphenyl, 4-hydroxyphenyl, $(CH_3)_2NCH_2$—, $(CH_3)_2CHCH(NH_2)$—, $HOCH_2CH_2NH$—, $CH_3OCH_2O$—, $CH_3OCH_2CH_2O$—, 2-pyrrolyl, 2-pyridyl, 3-pyridyl, 4-pyridyl, 1-methyl-1,4-dihydro-3-pyridyl, 2-pyrazinyl, 2-quinolyl, 3-quinolyl, 4-quinolyl, 1-isoquinolyl, 3-isoquinolyl, 2-quinoxalinyl, a phenyl group of formula

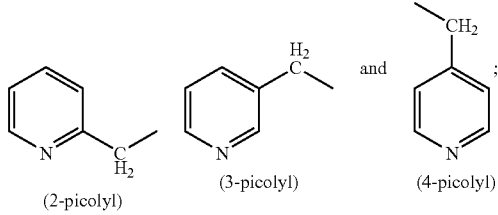

III a picolyl group selected from the group consisting of

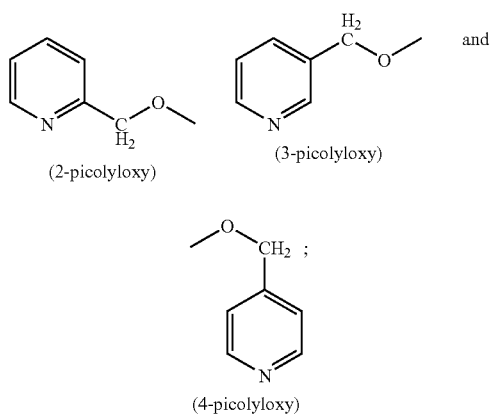

(2-picolyl)  (3-picolyl)  (4-picolyl)

a picolyloxy group selected from the group consisting of (2-picolyloxy)  (3-picolyloxy)

(4-picolyloxy)

a substituted pyridyl group selected from the group consisting of

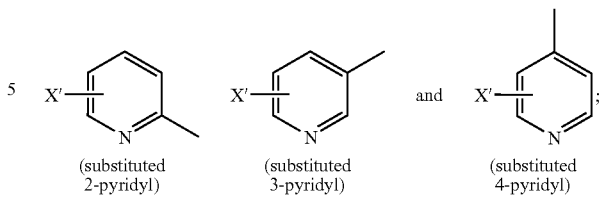

(substituted 2-pyridyl)  (substituted 3-pyridyl)  (substituted 4-pyridyl)

and a group of formula

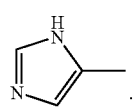

2. A method according to claim 1, wherein the compound is Formula IIa,

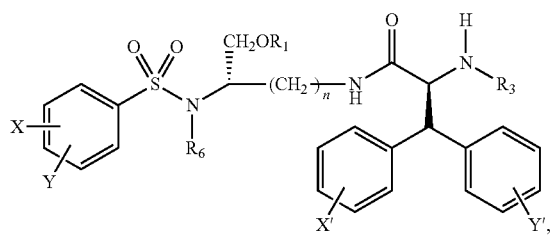

IIa or a pharmaceutically acceptable salt thereof.

3. A method according to claim 2, wherein $R_6$ is iso-butyl.

4. A method according to claim 3, wherein n is 4.

5. A method according to claim 4, wherein $R_1$ is $(HO)_2P(O)$ or $(NaO)_2P(O)$.

6. A method according to claim 1, wherein the compound is Formula IIb,

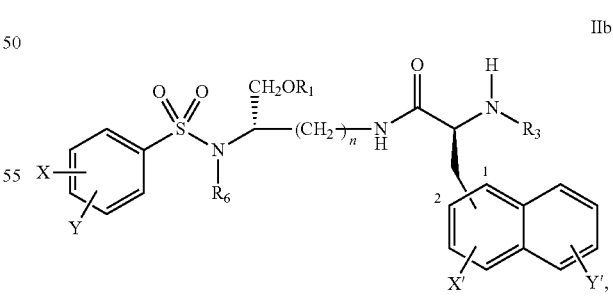

IIb or a pharmaceutically acceptable salt thereof.

7. A method according to claim 6, wherein $R_6$ is iso-butyl.

8. A method according to claim 7, wherein n is 4.

9. A method according to claim 8, wherein $R_1$ is $(HO)_2P(O)$ or $(NaO)_2P(O)$.

10. A method according to claim 1, wherein the compound is Formula IIc,

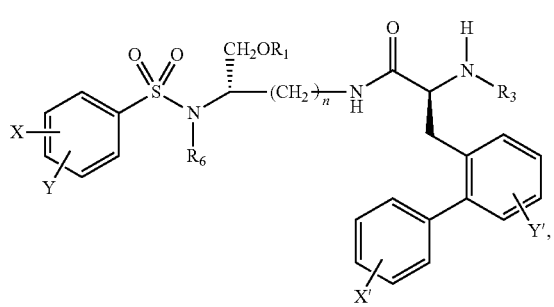

or a pharmaceutically acceptable salt thereof.

11. A method according to claim 10, wherein $R_6$ is isobutyl.

12. A method according to claim 11, wherein n is 4.

13. A method according to claim 12, wherein $R_1$ is $(HO)_2P(O)$ or $(NaO)_2P(O)$.

14. A method according to claim 5, wherein the compound is
(1S,5S)-(1-{5-[(4-amino-benzenesulfonyl)-isobutyl-amino]-6-phosphonooxy-hexacarbomoyl}-2,2-diphenyl-ethyl)-carbamic acid methyl ester or a pharmaceutically acceptable salt thereof; or
(1S,5S)-(1-{5-[(4-amino-3-fluoro-benzenesulfonyl)-isobutyl-amino]-6-phosphonooxy-hexacarbomoyl}-2,2-diphenyl-ethyl)-carbamic acid methyl ester or a pharmaceutically acceptable salt thereof.

15. A method according to claim 14, wherein the compound is (1S,5S)-(1-{5-[(4-amino-benzenesulfonyl)-isobutyl-amino]-6-phosphonooxy-hexacarbomoyl}-2,2-diphenyl-ethyl)-carbamic acid methyl ester sodium salt.

16. A method according to claim 14, wherein the compound is (1S,5S)-(1-{5-[(4-amino-3-fluoro-benzenesulfonyl)-isobutyl-amino]-6-phosphonooxy-hexacarbomoyl}-2,2-diphenyl-ethyl)-carbamic acid methyl ester sodium salt.

17. A method according to claim 1, wherein the compound Formula II is administered in combination with an HIV antiviral or anti-retroviral agent that targets attachment to the cell receptor and cell entry, reverse transcription or viral DNA integration.

18. A method according to claim 2, wherein the compound of Formula IIa is administered in combination with an HIV antiviral or anti-retroviral agent that targets attachment to the cell receptor and cell entry, reverse transcription or viral DNA integration.

19. A method according to claim 18, wherein the compound is
(1S,5S)-(1-{5-[(4-amino-benzenesulfonyl)-isobutyl-amino]-6-phosphonooxy-hexacarbomoyl}-2,2-diphenyl-ethyl)-carbamic acid methyl ester or a pharmaceutically acceptable salt thereof; or
(1S,5S)-(1-{5-[(4-amino-3-fluoro-benzenesulfonyl)-isobutyl-amino]-6-phosphonooxy-hexacarbomoyl}-2,2-diphenyl-ethyl)-carbamic acid methyl ester or a pharmaceutically acceptable salt thereof.

20. A method according to claim 1, wherein the compound of Formula II is administered in combination with another HIV protease inhibitor.

21. A method according to claim 2, wherein the compound of Formula IIa is administered in combination with another HIV protease inhibitor.

22. A method for treating or preventing viral infections that use aspartyl protease in their life cycle, which comprises administering a compound of Formula II,

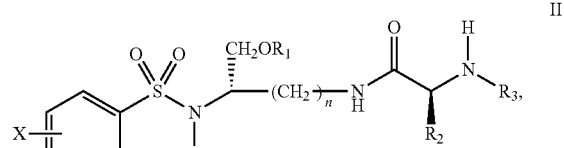

or a pharmaceutically acceptable salt thereof, wherein n is 3 or 4, wherein X and Y, the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_4R_5$, —NH-$COR_4$, —$OR_4$, —$COOR_4$, —$COR_4$, and —$CH_2OH$ or X and Y together define an alkylenedioxy group selected from the group consisting of a methylenedioxy group of formula —$OCH_2O$— and an ethylenedioxy group of formula —$OCH_2CH_2O$—, wherein $R_6$ is selected from the group consisting of a straight alkyl group of 1 to 6 carbon atoms, a branched alkyl group of 3 to 6 carbon atoms and a cycloalkylalkyl group having 3 to 6 carbon atoms in the cycloalkyl part thereof and 1 to 3 carbon atoms in the alkyl part thereof, wherein $R_3$ is selected from the group consisting of H, a straight alkyl group of 1 to 6 carbon atoms, a branched alkyl group of 3 to 6 carbon atoms, a cycloalkyl group of 3 to 6 carbon atoms, and a group of formula $R_{3A}$—CO—, $R_{3A}$ being selected from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part thereof and 1 to 3 carbon atoms in the alkyl part thereof, an alkyloxy group of 1 to 6 carbon atoms, tetrahydro-3-furanyloxy, —$CH_2OH$, —$CF_3$, —$CH_2CF_3$, —$CH_2CH_2CF_3$, pyrrolidinyl, piperidinyl, 4-morpholinyl, $CH_3O_2C$—, $CH_3O_2CCH_2$—, Acetyl-$OCH_2CH_2$—, $HO_2CCH_2$—, 3-hydroxyphenyl, 4-hydroxyphenyl, 4-$CH_3OC_6H_4CH_2$—, $CH_3NH$—, $(CH_3)_2N$—, $(CH_3CH_2)_2N$—, $(CH_3CH_2CH_2)_2N$—, $HOCH_2CH_2NH$—, $CH_3OCH_2O$—, $CH_3OCH_2CH_2O$—, $C_6H_5CH_2O$—, 2-pyrrolyl, 2-pyridyl, 3-pyridyl, 4-pyridyl-, 2-pyrazinyl, 2-quinolyl, 3-quinolyl, 4-quinolyl, 1-isoquinolyl, 3-isoquinolyl, 2-quinoxalinyl, a phenyl group of formula

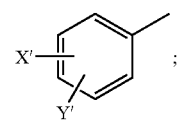

a picolyl group selected from the group consisting of

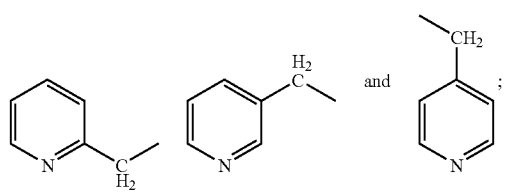

a picolyloxy group selected from the group consisting of

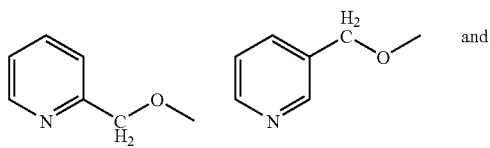

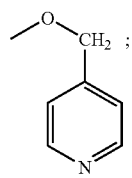

a substituted pyridyl group selected from the group consisting of

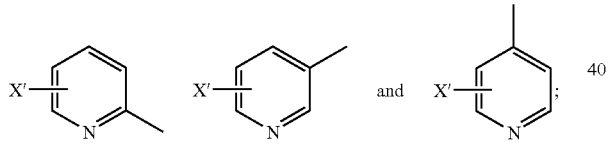

and a group of formula

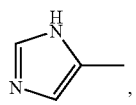

wherein X' and Y', the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —CF$_3$, —NO$_2$, —NR$_4$R$_5$, —NHCOR$_4$, —OR$_4$, —SR$_4$, —COOR$_4$, —COR$_4$ and —CH$_2$OH, wherein R$_4$ and R$_5$, the same or different, are selected from the group consisting of H, a straight alkyl group of 1 to 6 carbon atoms, a branched alkyl group of 3 to 6 carbon atoms, and a cycloalkyl group of 3 to 6 carbon atoms, wherein R$_2$ is selected from the group consisting of a diphenylmethyl group of formula IV,

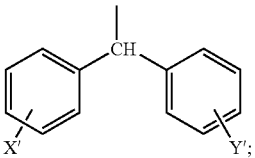

a naphthyl-1-CH$_2$— group of formula V,

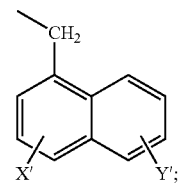

a naphthyl-2-CH$_2$— group of formula VI,

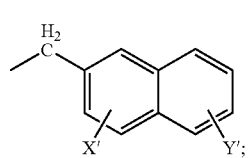

a biphenylmethyl group of formula VII,

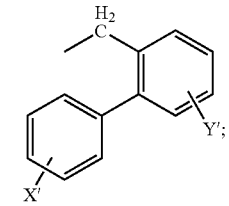

and an anthryl-9-CH$_2$— group of formula VIII,

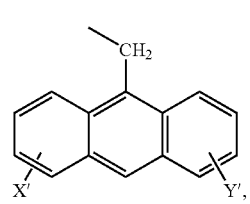

and wherein R$_1$ is selected from the group consisting of (HO)$_2$P(O), (MO)$_2$P(O) and a group of formula R$_{14}$—CO—, wherein M is an alkali metal or alkaline earth metal, wherein R$_{14}$ is selected from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part thereof and 1 to 3 carbon atoms in the alkyl part thereof, an alkyloxy group of 1 to 6 carbon atoms, —CH$_2$OH, CH$_3$O$_2$C—, CH$_3$O$_2$CCH$_2$—, Acetyl-OCH$_2$CH$_2$—, HO$_2$CCH$_2$—, 2-hydroxyphenyl, 3-hydroxyphenyl, 4-hydroxyphenyl, (CH$_3$)$_2$NCH$_2$—, (CH$_3$)$_2$CHCH(NH$_2$)—, HOCH$_2$CH$_2$NH—, CH$_3$OCH$_2$O—, CH$_3$OCH$_2$CH$_2$O—, 2-pyrrolyl, 2-pyridyl, 3-pyridyl, 4-pyridyl, 1-methyl-1,4-dihydro-3-pyridyl, 2-pyrazinyl, 2-quinolyl, 3-quinolyl, 4-quinolyl, 1-isoquinolyl, 3-isoquinolyl, 2-quinoxalinyl, a phenyl group of formula

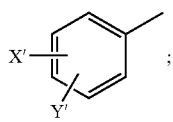

III a picolyl group selected from the group consisting of

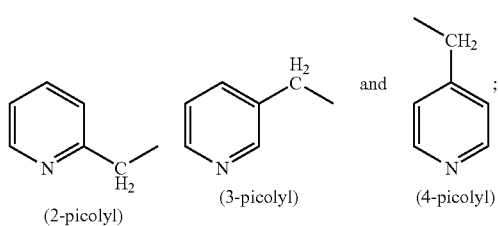

(2-picolyl)    (3-picolyl)    (4-picolyl)

a picolyloxy group selected from the group consisting of

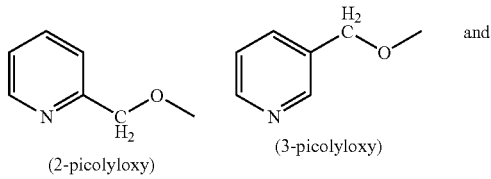

(2-picolyloxy)    (3-picolyloxy)

-continued

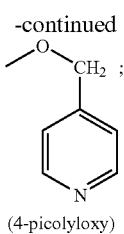

(4-picolyloxy)

a substituted pyridyl group selected from the group consisting of

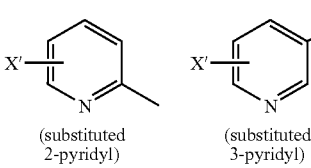

(substituted 2-pyridyl)    (substituted 3-pyridyl)    (substituted 4-pyridyl)

and a group of formula

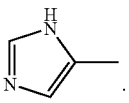

23. A method according to claim 22, wherein said viral infection is selected form the group consisting of simian immunodeficiency virus, HIV-2, HTLV-I and HTLV-II infections.

* * * * *